US011162113B2

(12) United States Patent
Harriman et al.

(10) Patent No.: US 11,162,113 B2
(45) Date of Patent: Nov. 2, 2021

(54) PLANTS COMPRISING A GIBBERELLIC ACID 2-OXIDASE GENE EXPRESSION CASSETTE

(71) Applicant: OMS Investments, Inc., Los Angeles, CA (US)

(72) Inventors: Robert Harriman, Delaware, OH (US); Lisa Lee, Marysville, OH (US); Rebecca Torisky, Marysville, OH (US)

(73) Assignee: OMS INVESTMENTS, INC., Los Angeles, CA (US)

(*) Notice: Subject to any disclaimer, the term of this patent is extended or adjusted under 35 U.S.C. 154(b) by 194 days.

(21) Appl. No.: 16/705,540

(22) Filed: Dec. 6, 2019

(65) Prior Publication Data

US 2020/0095601 A1 Mar. 26, 2020

Related U.S. Application Data

(62) Division of application No. 14/904,520, filed as application No. PCT/US2014/046536 on Jul. 14, 2014, now Pat. No. 10,501,753.

(60) Provisional application No. 61/985,238, filed on Apr. 28, 2014, provisional application No. 61/845,794, filed on Jul. 12, 2013.

(51) Int. Cl.

| | |
|---|---|
| ***C12N 15/82*** | (2006.01) |
| ***A01H 5/12*** | (2018.01) |
| ***A01N 57/20*** | (2006.01) |
| ***C12N 9/02*** | (2006.01) |
| ***C12N 9/10*** | (2006.01) |
| ***C12Q 1/6895*** | (2018.01) |

(52) U.S. Cl.

CPC ........... *C12N 15/8297* (2013.01); *A01H 5/12* (2013.01); *A01N 57/20* (2013.01); *C12N 9/0071* (2013.01); *C12N 9/1092* (2013.01); *C12N 15/8275* (2013.01); *C12Q 1/6895* (2013.01); *C12Y 114/11013* (2013.01); *C12N 2800/10* (2013.01); *C12Q 2600/13* (2013.01); *C12Q 2600/156* (2013.01); *C12Y 205/01019* (2013.01)

(58) Field of Classification Search

CPC .................................................. C12N 15/8297

See application file for complete search history.

(56) References Cited

U.S. PATENT DOCUMENTS

2014/0059714 A1* 2/2014 Matarasso .......... C12N 15/8246 800/281

OTHER PUBLICATIONS

GenBank Accession No. X51910, submitted on Feb. 16, 1990.*

* cited by examiner

*Primary Examiner* — Mykola V. Kovalenko
(74) *Attorney, Agent, or Firm* — Arent Fox LLP

(57) ABSTRACT

The invention provides for an expression cassette comprising a gibberellic acid 2-oxidase gene, and turfgrass plants comprising said cassette.

6 Claims, 6 Drawing Sheets

Specification includes a Sequence Listing.

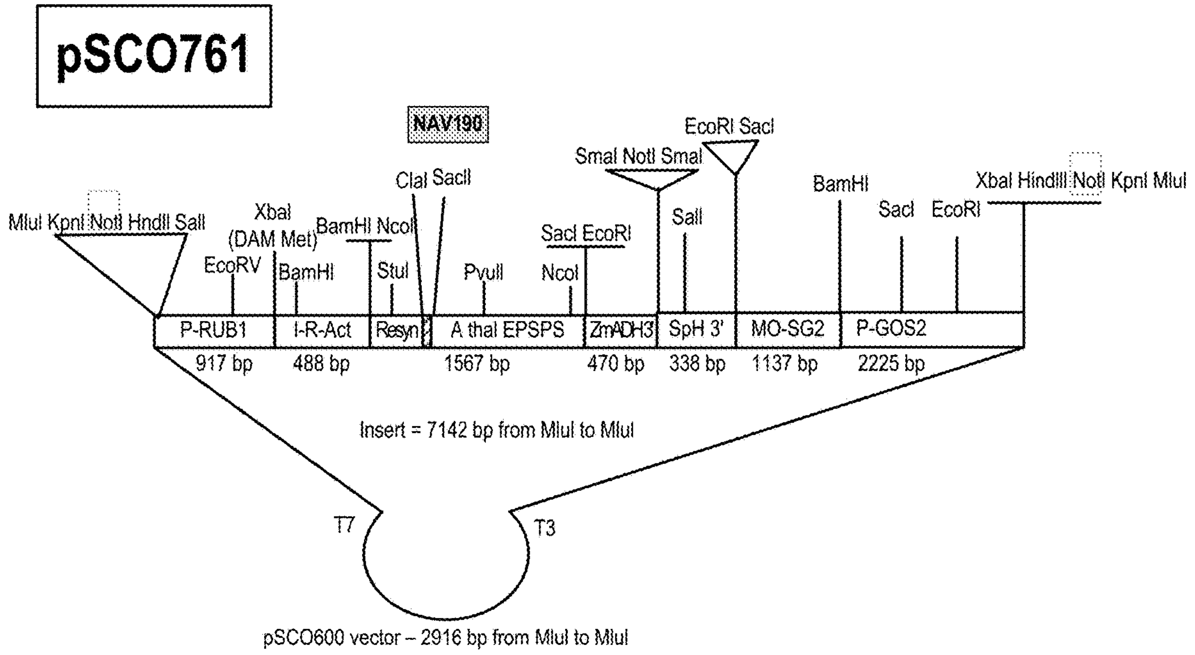
pSCO761
NAV190
EcoRI SacI
SmaI NotI SmaI
ClaI SacII
BamHI
XbaI HindIII NotI KpnI MluI
MluI KpnI NotI HndII SalI
XbaI
(DAM Met)
BamHI NcoI
SacI EcoRI
SalI
SacI
EcoRI
EcoRV
BamHI
StuI
PvuII
NcoI
P-RUB1
I-R-Act
Resyn
A thal EPSPS
ZmADH3'
SpH 3'
MO-SG2
P-GOS2
917 bp
488 bp
1567 bp
470 bp
338 bp
1137 bp
2225 bp
Insert = 7142 bp from MluI to MluI
T7
T3
pSCO600 vector – 2916 bp from MluI to MluI GTATCCACACATACGTTCTGAAAAACTGTGCACGTCCAAGAGGTTTCTTTCAATACAGAGGACTG
TAGTCATTATCAGCTCGGAAAGCTTTCTCCGCTTCTTCATCCCTCCACCTCTTCTGCTCTTTTTA
GATGATGTACGGTTTTGAAGCTTGTCAACCTTTTGTACCCGTGTAGAAAATTTTGAGTTTTCCCA
TGTACTCTTCTCTTTAAGAAGGCACGGCGGCTTCCACGAAGATGGTGGAACAATACGGCAAATCC
CATATGGTTCTGCTGTTGGCCGTATACTCTCAATATATTTTAGAGTGTCTTTAAATTCCTGATCC
ACGTAGAGAATATACCATAAGATTGGGCTATTTAGTAAAACAACAGAGATAGATAAAACGTGATA
CGGCAGTTAGCAAAGACGGAAGGTACCTCCTCAGTAGGATAGTAGACAGGAGCTTCGTCAAGAAC
AGGCCTCCGTGCACCAGCTGGATTCCAATTTGCAGTAACCTGCATGGTGTGAAAACACATAAGAC
AACAAGAGACCAGCTTCATGGAAGTAGGAAACACAGGAATTCAGCAGACGAATGTGAACCTTTTG
ACAGTCACTGCAGCCTGCACATCCTCGAATAACTCCTTTTGGTAATTTCTGTCTGCGCTTCGCTG
GACTTACAGCCTGCCAAAAGAACATTTTCATATAGTGGAAAGCATTAAAATCACAGTCATCTGTA
TTCTA*TGGTACCGCGGCCGCAAGCTTGTCGACCTGATGATTATTTGTTGATCAT*
(SEQ ID NO: 7)

FIG 2

GTATCATGGTATGGGATCACTAGATATTTTTCCACACAAGCAAACGTCACAAACTGCCGTGGTTC
GCATTCATCCACCAAACACACACACATCATCCACTGTGCTAAGCAGGCAGCCAAGCTGCTGAATG
GATGAACAGGGATCATGCCCGCGTACTCCAGATCGGACAGATTGATTTGGTGGCCTGTTGCGGTG
CAGCTGCTCGCTTGCGTCCGTGCGCGGTCTGGGCAGATCAAAACAGGGCTAGGTGGATGGCTGGC
TCGGCTGTCGGCTGGGCGCACCGGCGCAGCGACCAAAACGGAGGACTGGAGGAGGTGGGGACGCC
CTCGCGGACGAGCGGAGCAGAGGACCTTGGCGCGTGGACTCCCAGCCAGACCCCCGGTGAGGCGA
GGAGCTGTTGGACGTTACTCGGGAGCGAGCAGAGCAGCGATGCTGCCGCCGTCGGCAGCGGAGCT
AGGGGAGCAGGGAAAGCGCCGGTGAGGAGCGGGTCGGCAGACAACTCAAACGAGAAGAGGGAGAG
AGGAAGAAAGGCGGCGGCGCTCAGAACTCAGATGCGAGAGGCGGGGCGACCTGCTAGTGGACGCG
GTGGTCTGCCAGCAGCGCGGCGAGGCGAGGAAGTGAGGGAGGGCAATGGCGTGGGGAGGCGACAC
GCACGTGAGACTGTGAGAGACGGCGGCGTTCGCTCGCGTTTGGGAGGAAGGCAGCTAACAATTGA
TCTTGTCCGTCCGCAAAT*CGTGGTACCGCGGCCGC*AAGCTTTCTAGAATCCGAAAAGTTTCTGCA
CCGTTTTCACCCCCTAACTAACAATATAGGGAACGTGTGCTAATATAAAATG
(SEQ ID NO: 8

FIG 3

TCATCATCGCAGCAGATGATGGCCCAGGACCCAGGTTTCGCGCTTTGAACTGTGACGCTGTGCAA
GTTTGGTTGTCAAACTAGAACTGCAGCCACCCGTAAATTTGCAAGCAGCGGCAATCATGAGGTGT
GCGACTTCAGTGTGTCCCAGCTATCGCGTGTCTATTGAATGGCGAGACCTGATTCATTTTTTAAG
CATCATGGTCCTGCCTAACTTAGTACTAATAGACTGAGAATCGGGTTGTTTGTTTTCCGAATATG
TGGAAATTTTGTGGATCAAGGAGTAGCTCTTTTGAGTTCCTTTGAAGTTTGGTTGATTCAGGCAT
CTGCGCGTGAGAGAACAAATGCGGCTTGTCATGTCACACTCACACCACGGACGAACCAGGACAAG
CAGCCCTCAGCCCCTCTATCCCAACCACGGCCTCGCCGGTGATGGACCGGGAGAGTGAGATGCTC
TTTAGCGACTCGTCGTGTTT*CTCAAGTCTA*GATCCGCCGCCGCCGGTAACCACCCCGCCCC
SEQ ID NO: 9)

FIG 4

SEQ ID NO:1 401 UBB1 Dil 3-1
= GTTCTGAAAAACTGTGCACGTCCAAGAGG

SEQ ID NO:2 401 UBB1 Dil 5-2
= CGGCCGCGGTACCATAGAATACAGA

FIG 5

SEQ ID NO:3 415 GOB 1 Dil 3-1
= CCACACAAGCAAACGTCACAAACTG

SEQ ID NO:4 415 GOB1 Dil 5-2
= GCGGCCGCGGTACCACGATTTGCGGAC

FIG 6

SEQ ID NO:5 469 GOB1 Dil 3-1
= CAAACTAGAACTGCAGCCACCCGTAAATTTG

SEQ ID NO:6 469 GOB1 Dil 5-5
= TAGACTTGAGAAACACGACGAGTCGCT

FIG 7

| Lane | DNA template: | Primers used in PCR: |
|---|---|---|
| 1 | Size markers (100 bp DNA ladder) | none |
| 2 | 10 ng KB control TC-derived genomic DNA | 401 UBB1 dil 5-2/3-1 |
| 3 | 10 ng Pp009-401 genomic DNA | 401 UBB1 dil 5-2/3-1 |
| 4 | 10 ng Pp009-415 genomic DNA | 401 UBB1 dil 5-2/3-1 |
| 5 | 10 ng Pp009-469 genomic DNA | 401 UBB1 dil 5-2/3-1 |
| 6 | 1 ng Pp009-401 + 49.5 ng ea Pp009-415 and Pp009-469 DNA | 401 UBB1 dil 5-2/3-1 |
| 7 | Size markers (100 bp DNA ladder) | none |
| 8 | 10 ng KB control Abbey TC-derived DNA | 415 GOB1 dil 5-2/3-1 |
| 9 | 10 ng Pp009-401 genomic DNA | 415 GOB1 dil 5-2/3-1 |
| 10 | 10 ng Pp009-415 genomic DNA | 415 GOB1 dil 5-2/3-1 |
| 11 | 10 ng Pp009-469 genomic DNA | 415 GOB1 dil 5-2/3-1 |
| 12 | 1 ng Pp009-415 + 49.5 ng ea Pp009-401 and Pp009-469 DNA | 415 GOB1 dil 5-2/3-1 |
| 13 | Size markers (100 bp DNA ladder) | none |
| 14 | 10 ng KB control Abbey TC-derived DNA | 469 GOB1 dil 5-5/3-1 |
| 15 | 10 ng Pp009-401 genomic DNA | 469 GOB1 dil 5-5/3-1 |
| 16 | 10 ng Pp009-415 genomic DNA | 469 GOB1 dil 5-5/3-1 |
| 17 | 10 ng Pp009-469 genomic DNA | 469 GOB1 dil 5-5/3-1 |
| 18 | 1 ng Pp009-469 + 49.5 ng ea Pp009-401 and Pp009-415 DNA | 469 GOB1 dil 5-5/3-1 |
| 19 | Size markers (100 bp DNA ladder) | none |

FIG 8

5'-3' SEQUENCE OF EPSPS CASSETTE, COLOR CODED (RUBQ PROMOTER, *RICE ACTIN INTRON*, EPSPS CODING SEQUENCE, ZmADH 3'UTR)

ACGCGTGGTACCGCGGCCGCAAGCTTGTCGACCTGATGATTATTTTGTTGATCATGATTTTCTTTTGGCTATTTGATTTTTTGAAAG
ATATTTTTTTCCCTGGGAAGACACCTATGGGACGAAGATATTATGTTATATATATATATATATATATATCACATCAGTCTCTGCACA
AAGTGCATCCTGGGCTGCTTCAATTATAAAGCCCCATTCACCACATTTGCTAGATAGTCGAAAAGCACCATCAATATTGAGCTTCAG
GTATTTTTGGTTGTGTTGTGGTTGGATTGATTCTAATATATACCAAATCAATATAATTCACTACCAAAATATACCATAGCCATCACA
ACTTTATTAATTTTGGTAGCTTAAGATGGTATATATAATAACCAATTAACAACTGATTCTAATTTTACTACGGCCCAGTATCTACCA
ATACAAAACAACGAGTATGTTTTCTTCCGTCGTAATCGTACACAGTACAAAAAAACCTGGCCAGCCTTTCTTGGGCTGGGGCTCTCT
TTCGAAAGGTCACAAAACGTACACGGCAGTAACGCCGCTTCGCTGCGTGTTAACGGCCACCAACCCCGCCGTGAGCAAACGGCATCA
GCTTTCCACCTCCTCGATATCTCCGCGGCGCCGTCTGGACCCGCCCCCTTTCCGTTCCTTTCTTTCCTTCTCGCGTTTGCGTGGTGG
GGACGGACTCCCCAAACCGCCTCTCCCTCTCTTTATTTGTCTATATTCTCACTGGGCCCCACCCACCGCACCCCTGGGCCCACTCAC
GAGTCCCCCCCTCCCCACCTATAAATACCCCACCCCCTCCTCGCCTCTTCCTCCATCAATCGAATCCCCAAAATCGCAGAGAAAAAA
AAATCTCCCCTCGAAGCGAAGCGTCGAATCGCCTTCTCAAGTCTAGA*TCCGCCGCCGCCGGTAACCACCCCGCCCCTCTCCTCTTTC*
*TTTCTCCGTTTTTTTTTTCCGTCTCGGTCTCGATCTTTGGCCTTGGTAGTTTGGGTGGGCGAGAGGCGGCTTCGTGCGCGCCCAGAT*
*CGGTGCGCGGGAGGGGCGGGATCTCGCGGCTGGGGCTCTCGCCGGCGTGGATCCGGCCCGGATCTCGCGGGGAATGGGGCTCTCGGA*
*TGTAGATCTGCGATCCGCCGTTGTTGGGGGAGATGATGGGGGGTTTAAAATTTCCGCCATGCTAAACAAGATCAGGAAGAGGGGAAA*
*AGGGCACTATGGTTTATATTTTTATATATTTCTGCTGCTTCGTCAGGCTTAGATGTGCTAGATCTTTCTTTCTTCTTTTTGTGGGTA*
*GAATTTGAATCCCTCAGCATTGTTCATCGGTAGTTTTTCTTTTCATGATTTGTGACAAATGCAGCCTCGTGCGGAGCTTTTTTGTAG*
*GTAGAAG*GGATCCATGGCCCAGGTGTCCCGCATCTGCAACGGCGTGCAGAACCCATCCCTCATCTCCAACCTCTCCAAGTCCTCCCA
GCGCAAGTCCCCACTCTCCGTGTCCCTCAAGACCCAGCAACACCCACGCGCCTACCCAATCTCCAGCTCCTGGGGCCTCAAGAAGTC
CGGCATGACCCTCATCGGCTCCGAGCTGCGCCCACTCAAGGTGATGTCCTCCGTGTCCACCGCCGAGAAGGCCTCCGAGATCGTGCT
CCAGCCAATCCGCGAGATTTCCGGCCTCATCAAGCTCCCAGGCTCCAAGTCCCTCTCCAACCGCATCCTCCTGCTCGCCGCTCTCTC
CGAGGGCACCACCGTGGTGGACAACCTGCTCAACTCCGACGACATCAACTACATGCTCGACGCCCTCAAGCGCCTCGGCCTCAACGT
GGAGACCGACTCCGAGAACAACCGCGCCGTGGTGGAGGGCTGCGGCGGCATCTTCCCAGCCTCCATCGATTCCAAGTCCGACATCGA
GCTGTACCTCGGCAACTCCGGCACCTGCATGAGGTCACTCACGGCGGCGGTCACCGCGGCTGGCGGCAACGCCTCCTACGTGCTCGA
CGGCGTGCCAAGGATGCGCGAGCGCCCAATCGGCGACCTCGTGGTGGGCCTCAAGCAACTCGGCGCCGACGTGGAGTGCACCCTCGG
CACCAACTGCCCACCAGTGCGCGTGAACGCCAACGGCGGCCTCCCAGGCGGCAAGGTGAAGCTCTCCGGCTCCATCTCCTCCCAGTA
CCTCACCGCCCTGCTCATGTCCGCCCCACTCGCCCTCGGCGACGTGGAGATCGAGATCGTGGACAAGCTCATCTCCGTGCCATACGT
GGAGATGACCCTCAAGCTCATGGAGCGCTTCGGCGTGTCCGTGGAGCACTCCGACAGCTGGGACCGCTTCTTCGTGAAGGGCGGCCA
GAAGTACAAGTCCCCAGGCAACGCCTACGTGGAGGGCGACGCCTCCTCCGCCTCCTACTTCCTCGCTGGCGCTGCCATCACCGGCGA
GACCGTGACCGTGGAGGGGTGCGGCACCACCAGCCTCCAAGGCGACGTGAAGTTCGCCGAGGTGCTCGAGAAGATGGGCTGCAAGGT
GTCCTGGACCGAGAACTCCGTGACCGTGACCGGCCCACCAAGGGACGCCTTCGGCATGAGGCACCTCCGCGCCATCGACGTGAACAT
GAACAAGATGCCAGACGTGGCCATGACCCTCGCCGTGGTGGCCCTCTTCGCCGACGGCCCAACCACCATCAGGGACGTGGCCAGCTG
GCGCGTGAAGGAGACCGAGCGCATGATCGCCATCTGCACCGAGCTGAGAAAGCTCGGCGCCACCGTCGAGGAGGGCTCCGACTACTG
CGTGATCACCCCACCAAAGAAGGTCAAGACCGCCGAGATCGACACCTACGACGACCACCGCATGGCGATGGCCTTCTCCCTCGCCGC
CTGCGCCGACGTGCCGATCACCATCAACGACCCAGGCTGCACCCGCAAGACCTTCCCAGACTACTTCCAGGTGCTCGAGCGCATCAC
CAAGCACTGAGCTCGAATTCAGCTTCATTGCAAGCTAGCTCCTCCTGCAGGGCAGGCATGTCGCACAGCAAATGGGCATGAAAAGTTGAAGGCGCTCCAGTCC
TCCAGCTTGTGTAGTACACAGTAGCAATAAAACGTTAGTGTTTGTCCTGTGCCCATCCTGTATTATTCTGTTCCAGGGTTTCACCTTTATCGTCAGTGTGTGGTCAGG
TTTCAACCCTTCTCAGAACAACCCCCTCCCAGAAAAAAAACAAAGGAAGAAGTTTGTGTCCAGGTTTCAGAATCCCCTGTCTGTAATTACCATTTTGCATGACAATAA
TGAGATACTGTAGATATTAATAATGTTCCAGACCTTCAAGGCCTCCCTCCCTCGCAAATTGCAGATTTACTTGAGGTATCATTCGGTATTCACAAAATGTAACGTAAA
TAGTAGTGATTAACACTCGATTACCAGCGATAGGCAGTTTGAATAAGACGGCCCGGGGCGGCCGCCCCGGG

SEQ ID NO: 10

FIG 9

5'-3' SEQUENCE OF GA2OX CASSETTE, COLOR CODED (GOS2 PROMOTER, GA2OX CODING SEQUENCE, SPH 3'UTR)

ACGCGTGGTACCGCGGCCGCAAGCTTTCTAGAATCCGAAAAGTTTCTGCACCGTTTTCACCCCCTAACTAACAATATAGGGAACGTG
TGCTAAATATAAAATGAGACCTTATATATGTAGCGCTGATAACTAGAACTATGCAAGAAAAACTCATCCACCTACTTTAGTGGCAAT
CGGGCTAAATAAAAAAGAGTCGCTACACTAGTTTCGTTTTCCTTAGTAATTAAGTGGGAAAATGAAATCATTATTGCTTAGAATATA
CGTTCACATCTCTGTCATGAAGTTAAATTATTCGAGGTAGCCATAATTGTCATCAAACTCTTCTTGAATAAAAAAATCTTTCTAGCT
GAACTCAATGGGTAAAGAGAGAGATTTTTTTTAAAAAAATAGAATGAAGATATTCTGAACGTATTGGCAAAGATTTAAACATATAAT
TATATAATTTTATAGTTTGTGCATTCGTCATATCGCACATCATTAAGGACATGTCTTACTCCATCCCAATTTTTATTTAGTAATTAA
AGACAATTGACTTATTTTTATTATTTATCTTTTTTCGATTAGATGCAAGGTACTTACGCACACACTTTGTGCTCATGTGCATGTGTG
AGTGCACCTCCTCAATACACGTTCAACTAGCAACACATCTCTAATATCACTCGCCTATTTAATACATTTAGGTAGCAATATCTGAAT
TCAAGCACTCCACCATCACCAGACCACTTTTAATAATATCTAAAATACAAAAAATAATTTTACAGAATAGCATGAAAAGTATGAAAC
GAACTATTTAGGTTTTTCACATACAAAAAAAAAAAGAATTTTGCTCGTGCGCGAGCGCCAATCTCCCATATTGGGCACACAGGCAAC
AACAGAGTGGCTGCCCACAGAACAACCCACAAAAAACGATGATCTAACGGAGGACAGCAAGTCCGCAACAACCTTTTAACAGCAGGC
TTTGCGGCCAGGAGAGAGGAGGAGAGGCAAAGAAAACCAAGCATCCTCCTCCTCCCATCTATAAATTCCTCCCCCCTTTTCCCCTCT
CTATATAGGAGGCATCCAAGCCAAGAAGAGGGAGAGCACCAAGGACACGCGACTAGCAGAAGCCGAGCGACCGCCTTCTTCGATCCA
TATCTTCCGGTCGAGTTCTTGGTCGATCTCTTCCCTCCTCCACCTCCTCCTCACAGGGTATGTGCCCTTCGGTTGTTCTTGGATTTA
TTGTTCTAGGTTGTGTAGTACGGGCGTTGATGTTAGGAAAGGGGATCTGTATCTGTGATGATTCCTGTTCTTGGATTTGGGATAGAG
GGGTTCTTGATGTTGCATGTTATCGGTTCGGTTTGATTAGTAGTATGGTTTTCAATCGTCTGGAGAGCTCTATGGAAATGAAATGGT
TTAGGGTACGGAATCTTGCGATTTTGTGAGTACCTTTTGTTTGAGGTAAAATCAGAGCACCGGTGATTTTGCTTGGTGTAATAAAAG
TACGGTTGTTTGGTCCTCGATTCTGGTAGTGATGCTTCTCGATTTGACGAAGCTATCCTTTGTTTATTCCCTATTGAACAAAAATAA
TCCAACTTTGAAGACGGTCCCGTTGATGAGATTGAATGATTGATTCTTAAGCCTGTCCAAAATTTCGCAGCTGGCTTGTTTAGATAC
AGTAGTCCCCATCACGAAATTCATGGAAACAGTTATAATCCTCAGGAACAGGGGATTCCCTGTTCTTCCGATTTGCTTTAGTCCCAG
AATTTTTTTTCCCAAATATCTTAAAAAGTCACTTTCTGGTTCAGTTCAATGAATTGATTGCTACAAATAATGCTTTTATAGCGTTAT
CCTAGCTGTAGTTCAGTTAATAGGTAATACCCCTATAGTTTAGTCAGGAGAAGAACTTATCCGATTTCTGATCTCCATTTTTAATTA
TATGAAATGAACTGTAGCATAAGCAGTATTCATTTGGATTATTTTTTTTATTAGCTCTCACCCCTTCATTATTCTGAGCTGAAAGTC
TGGCATGAACTGTCCTCAATTTTGTTTTCAAATTCACATCGATTATCTATCGATTATCCTCTTGTATCTACCTGTAGAAGTTTCTTT
TTGGTTATTCCTTGACTGCTTGATTACAGAAAGAAATTTATGAAGCTGTAATCGGGATAGTTATACTGCTTGTTCTTATGATTCATT
TCCTTTGTGCAGTTCTTGGTGTAGCTTGCCACTTTCACCAGCAAAGTTTCGGATCCATGGCCTCCACCAAGGTGGTCGAGCACCTCA
AGGAGAACGTCCTCTGGAAGCAGGCCATCATGGACCGCAACGCCAACATCTCCGACCCACCGTTCGAGGAGACCTACAAGAACCTCC
TGCTCAAGCACAACATCACCCCGCTCACCACCACCACGACCACGACGACCACCACGGCGACCATCGAGGTGAGGGATCTCCCACTCA
TCGACCTCTCCAGGCTCGTGGCCACCGCCGCCAAGGAGCGCGAGAACTGCAAGAGGGATATCGCCAACGCCTCCCGCGAGTGGGGCT
TCTTCCAGGTGGTGAACCACGGCATCCCGCATAGGATGCTCGAGGAGATGAACAAGGAGCAGGTCAAGGTGTTCCGCGAGCCGTTCA
ACAAGAAGAAGGGCGACAACTGCATGAACCTCAGGCTCTCCCCAGGCTCCTACAGGTGGGGCTCCCCGACCCCGAACTGCCTCTCCC
AGCTCTCCTGGTCCGAGGCCTTCCACATCCCGATGAACGACATCTGCTCCAACGCCCCGAGGAACATTGCCAACGGCAACCCGAACA
TCTCCAACCTCTGCTCCACCGTGAAGCAGTTCGCCACCACCGTGTCCGAGCTGGCCAACAAGCTCGCCAACATCCTCGTCGAGAAGC
TCGGCCATGACGAGCTGACCTTCATCGAGGAGAAGTGCTCCCCGAACACGTGCTACCTCAGGATGAACCGCTACCCGCCGTGCCCAA
AGTACTCCCACGTGCTCGGCCTCATGCCACATACCGACTCCGACTTCCTCACCATCCTCTACCAGGACCAGGTGGGCGGCCTCCAGC
TCGTGAAGGACGGCCGCTGGATTTCCGTGAAGCCGAACCCAGAGGCCCTCATCGTGAACATCGGCGACCTCTTCCAGGCCTGGTCTA
ACGGCGTGTACAAGTCCGTGGTGCATAGGGTGGTGGCCAACCCGAGGTTCGAGAGGTTCTCTACCGCCTACTTCCTCTGCCCGTCCG
GCGACGCCGTGATCCAGTCCTACCGCGAGCCGTCTATGTACCGCAAGTTCAGCTTCGGCGAGTACAGGCAGCAGGTCCAGCAGGACG
TGCGCGAGTTCGGCCACAAGATCGGCCTCTCCCGCTTCCTCATCTGCAACGAGCTCGAATTCGCATGGCGTGGGATAATACAGACTGTATATAG
GAGGAATAATGGTTTGCTGCTTGTAGCTCTGTAAATAGGAAAATGAAGCTCAGCTTTTACTTTCAGTCATCTAGTTCGGTAGTGTAGGTCGGGTTTGCTGAAGTTTGGT
TAATGAAGGCTCTGTGTCTCTGCAAATTAAGGCGTTGTTCTGTCAATAATCATCTTTTTTCTGCAACATGCTTTCTTTCAAATTTGCCGAGTTACTTTTGTAATGATCA
TTAATGGCATTGTATAATCATTGATTGGTCGACGATAATCAATTGCCTGTATCACAAATTCAAGACTT

SEQ ID NO: 11

FIG 10

PLANTS COMPRISING A GIBBERELLIC ACID 2-OXIDASE GENE EXPRESSION CASSETTE

CROSS-REFERENCE TO RELATED PATENT APPLICATIONS

This application is a divisional of U.S. patent application Ser. No. 14/904,520, filed Jan. 12, 2016, which is the national phase application of International Patent Application No. PCT/US2014/046536, filed Jul. 14, 2014, which claims the benefit of U.S. Provisional Patent Application No. 61/985,238, filed Apr. 28, 2014, and which claims the benefit of U.S. Provisional Patent Application No. 61/845,794, filed Jul. 12, 2013, the contents of each are hereby incorporated by reference in their entireties.

FIELD OF THE INVENTION

The invention relates to the field of plant molecular biology. More specifically, the invention relates to Kentucky bluegrass plant events Pp009-401, Pp009-415 and Pp009-469, plants, seeds, and plant material comprising these events, and methods for detecting the presence of the events. Turfgrasses comprising events Pp009-401, Pp009-415, and/or Pp009-469 possess desirable characteristics including glyphosate tolerance and enhanced turfgrass quality. The invention also relates to plants, seeds, and plant material comprising a variant enzyme 5-enolpyruvyl-3-phosphoshikimate synthase (EPSPS) transgene and methods for detecting the presence of the variant EPSPS transgene. Plants comprising the variant EPSPS transgene possess glyphosate tolerance.

BACKGROUND OF THE INVENTION

Kentucky bluegrass (*Poa pratensis* L.) is an important turf species in many areas of the world. Kentucky bluegrass is used on consumer lawns, sport fields, on golf courses and various managed turfgrass areas. The control of weeds in Kentucky bluegrass is particularly problematic. Annual grasses, such as crabgrass, foxtail, dallisgrass, and goosegrass must be controlled by use of a variety of herbicides including bensulide, dithiopyr, oxadiazon, fenoxaprop and prodiamine applied at specific rates, environmental conditions, and seasons. Results vary even when applied by experts.

N-phosphonomethylglycine, also known as glyphosate, is a well-known herbicide that has activity on a broad spectrum of plant species. Glyphosate is the active ingredient of Roundup® (Monsanto Co.), an herbicide having a desirably short half-life in the environment. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the enzyme 5-enolpyruvyl-3-phosphoshikimate synthase (EPSPS) found in plants.

Glyphosate tolerance is a desirable phenotype in various plants. Glyphosate tolerance can be achieved by the expression of bacterial EPSPS variants and plant EPSPS variants that have lower affinity for glyphosate and therefore retain their catalytic activity in the presence of glyphosate. (See, e.g., U.S. Pat. Nos. 5,633,435; 5,094,945; 4,535,060; and 6,040,497).

Plants comprising events that confer glyphosate tolerance are known in the art. For example, U.S. Pat. No. 7,569,747, incorporated by reference herein in its entirety, relates to bentgrass event ASR-368, glyphosate tolerant plants comprising ASR-368, and methods for detecting ASR-368. There is a need, however, for other grasses tolerant to glyphosate.

SUMMARY OF VARIOUS EMBODIMENTS OF THE INVENTION

The invention provides for glyphosate tolerant turf grasses (e.g., Kentucky bluegrass), methods of making glyphosate tolerant turf grasses, and methods of controlling weeds in a field comprising glyphosate tolerant turf grasses by treating the field with an effective amount of an herbicide comprising glyphosate. The invention also provides for turf grasses that have enhanced turfgrass quality (e.g., require less mowing, have a darker green color, and generate a thicker, fuller stand).

The invention provides Kentucky bluegrass transgenic events designated Pp009-401, Pp009-415, and Pp009-469. Representative seeds comprising events Pp009-401, Pp009-415, and Pp009-469 have been deposited with American Type Culture Collection (ATCC) as Accession Nos. PTA-120354, PTA-120353, and PTA-120355, respectively. In one aspect, the invention includes plants grown from, or obtainable from, seeds comprising events Pp009-401, Pp009-415, or Pp009-469. The invention also includes progeny plants, seeds, or regenerable parts of plants comprising events Pp009-401, Pp009-415, or Pp009-469. In a particular aspect, plant parts, such as bulb, tuber, crown, stem, tiller, cuttings including un-rooted cuttings, rooted cuttings, and callus cuttings or callus-generated plantlets; apical meristems, pollen, ovule, flowers, shoots, stolons, progagules, seeds, runners, corms, rhizomes, roots, and leaves may comprise events Pp009-401, Pp009-415 and Pp009-469. In another aspect, the invention provides for a Kentucky bluegrass plant, cell, plant part, or seed comprising event Pp009-401, event Pp009-415, or event Pp009-469.

In another aspect, the invention provides for DNA comprising the transgene/genomic junction regions contained in the genome of events Pp009-401, Pp009-415, or Pp009-469. In another aspect, the invention provides for genomic DNA comprising events Pp009-401, Pp009-415, or Pp009-469. In a particular aspect, the invention provides for an isolated DNA molecule comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, the complements thereof, or combinations thereof. In another aspect, the invention provides for a plant, plant cell, plant part, or seed comprising the DNA molecule of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, the complements thereof, or combinations thereof.

In another aspect, the invention provides for a plant, plant cell, plant part, or seed comprising a DNA molecule with at least 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, the complements thereof, or combinations thereof.

In a further aspect, a DNA molecule may have at least about 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13. In a further aspect, a kit may comprise a DNA molecule with at least about 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

The invention also provides an expression vector comprising a nucleotide encoding a DNA molecule with at least 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

In another aspect, the invention provides for an host cell comprising a DNA molecule with at least 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

The invention further provides for methods of expressing a DNA molecule with at least 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 in a host cell and collecting the expressed polypeptide.

The invention also provides for a polypeptide encoded by a DNA molecule may have at least about 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13.

In one aspect, the invention provides for a method of detecting the transgene/genomic junction region of events Pp009-401, Pp009-415, or Pp009-469 in a plant. In another aspect, the invention provides for a method of detecting genomic DNA comprising events Pp009-401, Pp009-415, or Pp009-469 in a plant. These methods may involve the use of primers or probes specific for the transgene/genomic junction of events Pp009-401, Pp009-415, or Pp009-469. In a particular aspect, the invention provides for a method of detection comprising amplifying DNA from a plant, plant cell, plant part, or seed using the primers described herein. In an alternative aspect, the invention provides for a method of detection comprising hybridizing DNA from a plant, plant cell, plant part, or seed with the probes described herein.

In another aspect, the invention provides for compositions and methods for detecting the presence of a transgene/genomic junction region from Kentucky bluegrass plant event Pp009-401. DNA molecules are provided that comprise the transgene/genomic junction DNA molecule comprising SEQ ID NO: 2, or complements thereof, wherein the junction molecule spans the insertion site that comprises a heterologous DNA inserted into the Kentucky bluegrass genome and the genomic DNA from the Kentucky bluegrass cell flanking the insertion site in Kentucky bluegrass event Pp009-401. A Kentucky bluegrass plant Pp009-401 and seed comprising these molecules is another aspect of this invention.

In another aspect, the invention provides for compositions and methods for detecting the presence of a transgene/genomic junction region from Kentucky bluegrass plant event Pp009-415. DNA molecules are provided that comprise the transgene/genomic junction DNA molecule comprising SEQ ID NO: 4, or complements thereof, wherein the junction molecule spans the insertion site that comprises a heterologous DNA inserted into the Kentucky bluegrass genome and the genomic DNA from the Kentucky bluegrass cell flanking the insertion site in Kentucky bluegrass event Pp009-415. A Kentucky bluegrass plant Pp009-415 and seed comprising these molecules is another aspect of this invention.

In another aspect, the invention provides for compositions and methods for detecting the presence of a transgene/genomic junction region from Kentucky bluegrass plant event Pp009-469. DNA molecules are provided that comprise the transgene/genomic junction DNA molecule comprising SEQ ID NO: 6, or complements thereof, wherein the junction molecule spans the insertion site that comprises a heterologous DNA inserted into the Kentucky bluegrass genome and the genomic DNA from the Kentucky bluegrass cell flanking the insertion site in Kentucky bluegrass event Pp009-469. A Kentucky bluegrass plant Pp009-469 and seed comprising these molecules is another aspect of this invention.

In another aspect, the invention provides for two DNA molecules (primers) that, when used together in a DNA amplification method, produce an amplicon diagnostic for Kentucky bluegrass event Pp009-401. In one aspect, the primers are derived from SEQ ID NO: 7. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 7, or the complement thereof, and the second DNA molecule is of similar length and comprises any portion of a 5' flanking Kentucky bluegrass genomic DNA region of SEQ ID NO: 7, or the complement thereof. In a particular aspect, the DNA primers comprise SEQ ID NO: 1 and SEQ ID NO: 2. In alternative aspect, the invention provides for a DNA probe that, when used in a DNA hybridization method, detects Kentucky bluegrass event Pp009-401. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 7. In a particular aspect, the DNA probe comprises SEQ ID NO: 2.

In another aspect, the invention provides for two DNA molecules (primers) that, when used together in a DNA amplification method, produce an amplicon diagnostic for Kentucky bluegrass event Pp009-415. In one aspect, the primers are derived from SEQ ID NO: 8. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 8, or the complement thereof, and the second DNA molecule is of similar length and comprises any portion of a 5' flanking Kentucky bluegrass genomic DNA region of SEQ ID NO: 8, or the complement thereof. In a particular aspect, the DNA primers comprise SEQ ID NO: 3 and SEQ ID NO: 4. In alternative aspect, the invention provides for a DNA probe that, when used in a DNA hybridization method, detects Kentucky bluegrass event Pp009-415. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 8. In a particular aspect, the DNA probe comprises SEQ ID NO: 4.

In another aspect, the invention provides for two DNA molecules (primers) that, when used together in a DNA amplification method, produce an amplicon diagnostic for Kentucky bluegrass event Pp009-469. In one aspect, the primers are derived from SEQ ID NO: 9. In another aspect, the first DNA molecule comprises at least 11, 12, 13, 14, 15, 16, 17, 18, 19, 20, 21, 22, 23, 24, 25, 26, 27, 28, 29, or more contiguous or homologous polynucleotides of any portion of the transgene region of the DNA molecule of SEQ ID NO: 9, or the complement thereof, and the second DNA molecule is of similar length and comprises any portion of a 5' flanking Kentucky bluegrass genomic DNA region of SEQ ID NO: 9, or the complement thereof. In a particular aspect, the DNA primers comprise SEQ ID NO: 5 and SEQ ID NO: 6. In alternative aspect, the invention provides for a DNA probe that, when used in a DNA hybridization method, detects Kentucky bluegrass event Pp009-469. In another aspect, the DNA probe comprises at least 11, 12, 13, 14, 15, 16, 17, 18, 19, 20, 21, 22, 23, 24, 25, 26, 27, 28, 29, or more nucleotides that hybridize to any portion of the transgene region and any portion of the flanking genomic DNA region of the DNA molecule of SEQ ID NO: 9. In a particular aspect, the DNA probe comprises SEQ ID NO: 6.

In another aspect, the invention provides for methods of detecting the presence of DNA corresponding specifically to the Kentucky bluegrass event Pp009-401, Pp009-415, or Pp009-469 DNA in a sample. These methods comprise: (a) contacting a DNA sample with a primer pair that, when used in a nucleic acid amplification reaction with genomic DNA from Kentucky bluegrass event Pp009-401, Pp009-415, or Pp009-469 produces an amplicon diagnostic for Kentucky bluegrass event Pp009-401, Pp009-415, or Pp009-469; (b) performing a nucleic acid amplification reaction, thereby producing the amplicon; and (c) detecting the amplicon.

In another aspect, the invention provides for methods of detecting the presence of DNA corresponding specifically to the Kentucky bluegrass event Pp009-401, Pp009-415, and Pp009-469 DNA in a sample. These methods comprise: (a) contacting a DNA sample with a probe that hybridizes under stringent hybridization conditions with genomic DNA from Kentucky bluegrass event Pp009-401, Pp009-415, or Pp009-469; (b) subjecting the sample and probe to stringent hybridization conditions; and (c) detecting hybridization of the probe to the Pp009-401, Pp009-415, or Pp009-469 DNA.

In another aspect, the invention provides for methods of producing a Kentucky bluegrass plant that tolerates application of glyphosate comprising sexually crossing a first parental Kentucky bluegrass event Pp009-401, Pp009-415, or Pp009-469 and a second parental plant (e.g., Kentucky bluegrass) that lacks Pp009-401, Pp009-415, or Pp009-469 (or that lacks glyphosate tolerance), thereby producing a plurality of progeny plants.

In another aspect, the invention provides for methods of producing a Kentucky bluegrass plant that tolerates application of glyphosate comprising: (a) sexually crossing a first parental Kentucky bluegrass event Pp009-401, Pp009-415, or Pp009-469 and a second parental plant (e.g., Kentucky bluegrass) that lacks Pp009-401, Pp009-415, or Pp009-469 (or that lacks glyphosate tolerance), thereby producing a plurality of progeny plants; and (b) selecting a progeny plant that tolerates application of glyphosate. Such methods may optionally comprise the further step of back-crossing the progeny plant to the second parental Kentucky bluegrass plant and selecting for glyphosate tolerant progeny to produce a true-breeding Kentucky bluegrass variety that tolerates application of glyphosate.

In another aspect, the invention provides for a turfgrass stand, lawn, sports field, or golf course comprising event Pp009-401, Pp009-415 and/or Pp009-469. In another aspect, the invention provides for a method of controlling weeds in a turfgrass stand of Kentucky bluegrass Pp009-401, Pp009-415 and/or Pp009-469 comprising the step of applying a glyphosate containing herbicide formulation to the turfgrass stand.

In another embodiment, the invention provides for methods of producing a Kentucky bluegrass plant that tolerates application of glyphosate comprising sexually crossing a first parental Kentucky bluegrass comprising the nucleic acid of SEQ ID NO: 10 or 12 and a second parental plant (e.g., Kentucky bluegrass) that lacks the nucleic acid of SEQ ID NO: 10 or 12 (or that lacks glyphosate tolerance), thereby producing a plurality of progeny plants.

In another embodiment, the invention provides for methods of producing a Kentucky bluegrass plant that tolerates application of glyphosate comprising: (a) sexually crossing a first parental Kentucky bluegrass the nucleic acid of SEQ ID NO: 10 or 12 and a second parental plant (e.g., Kentucky bluegrass) that lacks the nucleic acid of SEQ ID NO: 10 or 12 (or that lacks glyphosate tolerance), thereby producing a plurality of progeny plants; and (b) selecting a progeny plant that tolerates application of glyphosate. Such methods may optionally comprise the further step of back-crossing the progeny plant to the second parental Kentucky bluegrass plant and selecting for glyphosate tolerant progeny to produce a true-breeding Kentucky bluegrass variety that tolerates application of glyphosate.

In another embodiment, the invention provides for a turfgrass stand, lawn, sports field, or golf course comprising the nucleic acid of SEQ ID NO: 10 or 12. In another embodiment, the invention provides for a method of controlling weeds in a turfgrass stand of Kentucky bluegrass the nucleic acid of SEQ ID NO: 10 or 12 comprising the step of applying a glyphosate containing herbicide formulation to the turfgrass stand.

In one embodiment, a method for detecting the presence of genomic DNA, may comprise (1) amplifying a nucleic acid obtained from a Kentucky bluegrass plant, plant cell, or plant material using a primer pair of SEQ ID NO: 1 and SEQ ID NO: 2; or (2) hybridizing a nucleic acid obtained from a Kentucky bluegrass plant, plant cell, or plant material using a probe comprising SEQ ID NO: 1 and SEQ ID NO: 2.

In one embodiment, a method for detecting the presence of genomic DNA, may comprise (1) amplifying a nucleic acid obtained from a Kentucky bluegrass plant, plant cell, or plant material using a primer pair of SEQ ID NO: 3 and SEQ ID NO: 4; or (2) hybridizing a nucleic acid obtained from a Kentucky bluegrass plant, plant cell, or plant material using a probe comprising SEQ ID NO: 3 and SEQ ID NO: 4.

In one embodiment, a method for detecting the presence of genomic DNA, may comprise (1) amplifying a nucleic acid obtained from a Kentucky bluegrass plant, plant cell, or plant material using a primer pair of SEQ ID NO: 5 and SEQ ID NO: 6; or (2) hybridizing a nucleic acid obtained from a Kentucky bluegrass plant, plant cell, or plant material using a probe comprising SEQ ID NO: 5 and SEQ ID NO: 6.

In one embodiment, a kit may comprise the primer pair or probe of SEQ ID NO: 1 and SEQ ID NO: 2. In one embodiment, a kit may comprise the primer pair or probe of SEQ ID NO: 3 and SEQ ID NO: 4. In one embodiment, a kit may comprise the primer pair or probe of SEQ ID NO: 5 and SEQ ID NO: 6. In another embodiment, the primer pair or probe may be attached to a solid support. In another embodiment, the solid support may be a bead, fiber, plate, or multi-well plate. In another embodiment, the primer pair or probe may be arranged in an array. In another embodiment, the kit may further comprise a buffer or solution. In another embodiment, the primer pair or probe may be labeled. In another embodiment, the label may be a florescent molecule, a radioactive isotope, ligand, chemifluorescent, chemiluminescent agent, or enzyme.

In another embodiment, the method for producing Kentucky bluegrass plant or seed may comprise selfing or crossing a Kentucky bluegrass plant comprising event Pp009-401, event Pp009-415, or event Pp009-469 with a plant lacking event Pp009-401, event Pp009-415, or event Pp009-469, and planting seed obtained from said cross.

In one embodiment, an isolated nucleic acid may comprise the nucleotide sequence of SEQ ID NO: 10, SEQ ID NO: 11, SEQ ID NO: 12, or SEQ ID NO: 13. In another embodiment, an isolated nucleic acid may comprise the nucleotide sequence of SEQ ID NO: 10. In another embodiment, an isolated nucleic acid may comprise the nucleotide sequence of SEQ ID NO: 11. In another embodiment, an isolated nucleic acid may comprise the nucleotide sequence of SEQ ID NO: 12. In another embodiment, an isolated nucleic acid may comprise the nucleotide sequence of SEQ ID NO: 13.

In one embodiment, an isolated cassette may comprise the nucleotide sequence of SEQ ID NO: 10 or SEQ ID NO: 11. In another embodiment, an isolated cassette may comprise the nucleotide sequence of SEQ ID NO: 10. In another embodiment, an isolated cassette may comprise the nucleotide sequence of SEQ ID NO: 11.

In one embodiment, an isolated plasmid may comprise the nucleotide sequence of SEQ ID NO: 10, SEQ ID NO: 11, SEQ ID NO: 12, or SEQ ID NO: 13. In another embodiment, an isolated plasmid may comprise the nucleotide sequence of SEQ ID NO: 10. In another embodiment, an isolated plasmid may comprise the nucleotide sequence of SEQ ID NO: 11. In another embodiment, an isolated plasmid may comprise the nucleotide sequence of SEQ ID NO: 12. In another embodiment, an isolated plasmid may comprise the nucleotide sequence of SEQ ID NO: 13.

In one embodiment, an isolated cell may comprise the nucleotide sequence of SEQ ID NO: 10, SEQ ID NO: 11, SEQ ID NO: 12, or SEQ ID NO: 13. In another embodiment, an isolated cell may comprise the nucleotide sequence of SEQ ID NO: 10. In another embodiment, an isolated cell may comprise the nucleotide sequence of SEQ ID NO: 11. In another embodiment, an isolated cell may comprise the nucleotide sequence of SEQ ID NO: 12. In another embodiment, an isolated cell may comprise the nucleotide sequence of SEQ ID NO: 13. In another embodiment, the cell may be a bacterial cell or a plant cell.

In one embodiment, a Kentucky bluegrass plant, cell, plant part, or seed may comprise the nucleotide sequence of SEQ ID NO: 10, SEQ ID NO: 11, SEQ ID NO: 12, or SEQ ID NO: 13. In another embodiment, a seed of Kentucky bluegrass may comprise the nucleotide sequence of SEQ ID NO: 10, SEQ ID NO: 11, SEQ ID NO: 12, or SEQ ID NO: 13. In another embodiment, a Kentucky bluegrass plant, or part thereof, may produced from a seed comprising the nucleotide sequence of SEQ ID NO: 10, SEQ ID NO: 11, SEQ ID NO: 12, or SEQ ID NO: 13. In another embodiment, the part may be a cell, bulb, tuber, crown, stem, tiller, cuttings including un-rooted cuttings, rooted cuttings, and callus cuttings or callus-generated plantlets; apical meristems, pollen, ovule, flower, shoot, stolon, progagule, seed, runner, corm, rhizome, root, or leaf.

In one embodiment, a method for producing Kentucky bluegrass plant or seed may comprise growing the seed comprising the nucleotide sequence of SEQ ID NO: 10, SEQ ID NO: 11, SEQ ID NO: 12, or SEQ ID NO: 13.

In one embodiment, the method for controlling weeds in a field may comprise growing the seed comprising the nucleotide sequence of SEQ ID NO: 10, SEQ ID NO: 11, SEQ ID NO: 12, or SEQ ID NO: 13 and treating the field with an effective amount of an herbicide comprising glyphosate.

In one embodiment, a lawn may comprise a plant comprising the nucleotide sequence of SEQ ID NO: 10, SEQ ID NO: 11, SEQ ID NO: 12, or SEQ ID NO: 13.

In one embodiment, a method for producing a Kentucky bluegrass plant that tolerates application of glyphosate may comprise sexually crossing a first parental Kentucky bluegrass comprising the nucleic acid of SEQ ID NO: 10 or 12 and a second parental plant that lacks the nucleic acid of SEQ ID NO: 10 or 12 or that lacks glyphosate tolerance, thereby producing a plurality of progeny plants.

In one embodiment, a method for producing a Kentucky bluegrass plant that tolerates application of glyphosate may comprise: (a) sexually crossing a first parental Kentucky bluegrass the nucleic acid of SEQ ID NO: 10 or 12 and a second parental plant that lacks the nucleic acid of SEQ ID NO: 10 or 12 or that lacks glyphosate tolerance, thereby producing a plurality of progeny plants; and (b) selecting a progeny plant that tolerates application of glyphosate. In another embodiment, the method may further comprise back-crossing the progeny plant to the second parental Kentucky bluegrass plant and selecting for glyphosate tolerant progeny to produce a true-breeding Kentucky bluegrass variety that tolerates application of glyphosate.

In one embodiment, a turfgrass stand, lawn, sports field, or golf course may comprise a Kentucky bluegrass plant comprising the nucleic acid of SEQ ID NO: 10 or 12.

In one embodiment, a method of controlling weeds in a turfgrass stand of Kentucky bluegrass the nucleic acid of SEQ ID NO: 10 or 12 may comprise the step of applying a glyphosate containing herbicide formulation to the turfgrass stand.

In one embodiment, a plant cell may comprise the nucleotide sequence of SEQ ID NO: 10, SEQ ID NO: 11, SEQ ID NO: 12, or SEQ ID NO: 13.

In one embodiment, a plant cell may comprise the event Pp009-401, event Pp009-415, or event Pp009-469.

In one embodiment, a plant may comprise the event Pp009-401, event Pp009-415, or event Pp009-469.

In one embodiment, a plant may comprise the nucleotide sequence of SEQ ID NO: 10, SEQ ID NO: 11, SEQ ID NO: 12, or SEQ ID NO: 13.

In one embodiment, a transgenic plant may comprise the nucleotide sequence of SEQ ID NO: 10. In one embodiment, a transgenic plant may comprise the nucleotide sequence of SEQ ID NO: 11. In one embodiment, a transgenic plant may comprise the nucleotide sequence of SEQ ID NO: 12. In one embodiment, a transgenic plant may comprise the nucleotide sequence of SEQ ID NO: 13.

In one embodiment, the plant may be a grass, grain crop, an agricultural crop, ornamental flower, legume, fruit, vegetable, herb, ornamental flower, perennial plant, or tree.

In one embodiment, the plant may be a grass. In another embodiment, the grass may be Bahia grass, bent grass, Bermuda grass, Blue grama grass, Buffalo grass, centipedes grasses, fescue grass, optionally needle-leaved Fescue grass, tall Fescue, or broad-leaved Fescue grass, Kentucky bluegrass, rygrass optionally annual ryegrass or perennial ryegrass, seashore *paspalum*, St. Augustine grass, or *Zoysia* grass.

In another embodiment, the plant may be a grain crop. In another embodiment, the grain crop may be barley, sorghum, millet, rice, canola, corn, oats, wheat, barley, or hops. In a further embodiment, the plant may be soybean.

In one embodiment, the plant may be an ornamental flower. In another embodiment, the flower may be an annual or perennial ornamental flower. In another embodiment, the ornamental flower may be a geranium, *petunia*, or daffodil.

In one embodiment, the plant may be a legume. In one embodiment, the legume may be alfalfa, clover, peas, beans, lentils, lupins, mesquite, carob, soybeans, peanuts, or tamarind.

In one embodiment, the plant may be a fruit. In another embodiment, the fruit may be a grape, raspberry, blueberry, strawberry, blackberry, watermelon, apple, cherry, pear, orange, lemon, or pumpkin.

In one embodiment, the plant may be a vegetable. In another embodiment, the vegetable may be asparagus, Brussels sprouts, cabbage, carrots, celery, chard, collard greens, endive, tomatoes, beans, peas, broccoli, cauliflower, bell pepper, eggplant, kale, lettuce, okra, onion, radish, spinach, peppers, broccoli, cucumber, zucchini, eggplant, beet, squash, beans, potato, or onion.

In one embodiment, the plant may be a herb. In another embodiment, the herb may be anise, basil, caraway, cilantro, chamomile, dill, fennel, lavender, lemon grass, marjoram, oregano, parsley, rosemary, sage, thyme, or mint.

In one embodiment, the plant may be a root vegetable or a vine vegetable. In another embodiment, the root vegetable may be a turnip, potato, carrot, or beet. In another embodiment, the vine vegetable may be a cucumber, pumpkin, squash, melon, or zucchini.

In one embodiment, the plant may be an agricultural crop. In another embodiment, the agricultural crop may be cotton, corn, sugar cane, wheat, soybean, tobacco, or citrus.

In one embodiment, the plant may be an ornamental plant. In another embodiment, the ornamental plant may be a geranium, *petunia*, impatien, *verbena*, dahlia, pansy, *vinca, ipomoea*, lantana, *salvia*, snapdragon, scaevola, torenia, *lobelia*, dipladenia, calibrachoa, asters, agerantum, *phlox*, penstemon, gaillardia, *zinnia, coleus*, osteospermum, *gerbera, begonia*, angelonia, *dianthus*, calendula, *campanula, celosia, portulaca*, viola, or mum. In another embodiment, the ornamental plant may be a variety of the *vinca* genus. In another embodiment, the ornamental plant may be a variety of the *Helianthus annuus* genus. In another embodiment, the ornamental plant may be a variety of the *Impatients hawkeri* genus. In another embodiment, the ornamental plant may be a variety of the *lantana* genus. In another embodiment, the ornamental plant may be a variety of the *Mandevilla hydrida* genus. In another embodiment, the ornamental plant may be a variety of the *pelargonium* interspecific genus. In another embodiment, the ornamental plant may be a variety of the *Pentas lanceolata* genus. In another embodiment, the ornamental plant may be a variety of the *Petunia pendula* genus. In another embodiment, the ornamental plant may be a variety of the *rudbeckia* genus. In another embodiment, the ornamental plant may be a variety of the *Tagetes erecta* genus. In another embodiment, the ornamental plant may be a variety of the *Viola cornuta* genus. In another embodiment, the ornamental plant may be a variety of the *Viola wittrockiana* genus. In another embodiment, the ornamental plant may be a variety of the *zinnia* genus.

In one embodiment, a plant, or part thereof, may be from a plant comprising the nucleic acid sequence of SEQ ID NO: 10, 11, 12, or 13. In another embodiment, the part may be a cell, bulb, tuber, crown, stem, tiller, cuttings including un-rooted cuttings, rooted cutting, and callus cutting or callus-generated plantlet; apical meristem, pollen, ovule, flower, shoot, stolon, progagule, seed, runner, corm, rhizome, root, or leaf.

In one embodiment, a method for controlling weeds in a field may comprise growing a seed from a plant comprising the nucleic acid sequence of SEQ ID NO: 12 or SEQ ID NO: 12 and SEQ ID NO: 13 and treating the field with an effective amount of an herbicide comprising glyphosate.

The foregoing and other aspects of the invention will become more apparent from the following detailed description and accompanying drawings.

BRIEF DESCRIPTION OF THE DRAWINGS

FIG. 1 depicts a plasmid map of pSCO761.

FIG. 2 depicts the Pp009-401 transgene/genomic/chromosomal flanking DNA sequence (SEQ ID NO: 7). The single underlined sequence represents the native DNA primer 401 UBB1 Dil 3-1 priming site. The double underlined sequence represents the pSCO761 junction primer 401 UBB1 Dil 5-2 priming site. The italicized sequence represents the pSCO761 transgene homology. The primers span a sequence of 720 bases in length (i.e., the primers produce an amplicon of 720 bp).

FIG. 3 depicts Pp009-415 transgene/genomic/chromosomal flanking DNA sequence (SEQ ID NO: 8). The single underlined sequence represents the native DNA primer 415 GOB1 Dil 3-1 priming site. The double underlined sequence represents the pSCO761 junction primer 415 GOB1 Dil 5-2 priming site. The italicized sequence represents the pSCO761 transgene homology. The primers span a sequence of 719 bases in length (i.e., the primers produce an amplicon of 719 bp).

FIG. 4 depicts Pp009-469 transgene/genomic/chromosomal flanking DNA sequence (SEQ ID NO: 9) The single underlined sequence represents the native DNA primer 469 GOB1 Dil 3-1 priming site. The double underlined sequence represents the pSCO761 junction primer 469 GOB1 Dil 5-5 priming site. The italicized sequence represents the pSCO761 transgene homology. The primers span a sequence of 410 bases in length (i.e., the primers produce an amplicon of 410 bp).

FIG. 5 depicts the 401 UBB1 Dil 3-1 primer sequence (SEQ ID NO: 1) and 401 UBB1 Dil 5-2 primer sequence (SEQ ID NO: 2). These primers are useful in detecting event Pp009-401.

FIG. 6 depicts the 415 GOB1 Dil 3-1 primer sequence (SEQ ID NO: 3) and 415 GOB1 Dil 5-2 primer sequence (SEQ ID NO: 4). These primers are useful in detecting event Pp009-415.

FIG. 7 depicts the 469 GOB1 Dil 3-1 primer sequence (SEQ ID NO: 5) and 469 GOB1 Dil 5-5 primer sequence (SEQ ID NO: 6). These primers are useful in detecting event p009-469.

FIG. 8 is a photograph of an electrophoresis gel showing PCR bands from reactions using primers disclosed herein.

FIG. 9 depicts the sequence of the EPSPS cassette comprising a RUBQ promoter (bold), rice actin intron (italicized), EPSPS coding sequence (underline), and ZmADH 3' UTR (SMALL CAPS). The EPSPS cassette comprises heterologous DNA sequences.

FIG. 10 depicts the sequence of the GA2OX cassette comprising a GOS2 promoter (bold), GA2OX coding sequence (underline), and SpH 3' UTR (SMALL CAPS). The GA2OX cassette comprises heterologous DNA sequences.

DETAILED DESCRIPTION OF PREFERRED EMBODIMENTS OF THE INVENTION

The invention provides Kentucky bluegrass plant events Pp009-401, Pp009-415 and Pp009-469, turfgrasses, plants, seeds, and plant material comprising these events, and methods for detecting the presence of the events. Plants (e.g., turfgrasses) may comprise events Pp009-401, Pp009-415, and/or Pp009-469 possess desirable characteristics including glyphosate tolerance and enhanced turfgrass quality. The invention also provides plants, bulb, tuber, crown, stem, tiller, cuttings including un-rooted cuttings, rooted cuttings, and callus cuttings or callus-generated plantlets; apical meristems, pollen, ovule, flowers, shoots, stolons, progagules, seeds, runners, corms, rhizomes, roots, leaves, and plant material comprising a variant enzyme 5-enolpyruvyl-3-phosphoshikimate synthase (EPSPS) transgene and methods for detecting the presence of the variant EPSPS transgene. Plants comprising the variant EPSPS transgene possess glyphosate tolerance. The invention also provides plants, bulb, tuber, crown, stem, tiller, cuttings including un-rooted cuttings, rooted cuttings, and callus cuttings or callus-generated plantlets; apical meristems, pollen, ovule, flowers, shoots, stolons, progagules, seeds, runners, corms, rhizomes, roots, leaves, and plant material comprising a gibberellic acid 2-oxidase (GA2OX) transgene and variant EPSPS transgene and methods for detecting the presence of the GA2OX transgene or variant EPSPS transgene. Plants comprising the variant GA2OX transgene may exhibit shorter stature, darker green color, thicker/more density, shorter stolons, better nutrient use efficiency, better water use efficiency. The invention also provides plants, bulb, tuber, crown, stem, tiller, cuttings including un-rooted cuttings, rooted cuttings, and callus cuttings or callus-generated plantlets; apical meristems, pollen, ovule, flowers, shoots, stolons, progagules, seeds, runners, corms, rhizomes, roots, leaves, and plant material comprising a variant enzyme 5-enolpyruvyl-3-phosphoshikimate synthase (EPSPS) transgene and a gibberellic acid 2-oxidase (GA2OX) transgene and methods for detecting the presence of the EPSPS and/or GA2OX transgenes.

Definitions

Unless otherwise indicated, all terms used herein have the same meaning as they would to one skilled in the art.

"Conservative substitution," as used herein, refers broadly to the substitution of an amino acid by another amino acid of the same class, in which the classes are defined as follows: Nonpolar: A, V, L, I, P, M, F, W Uncharged polar: G, S, T, C, Y, N, Q Acidic: D, E Basic: K, R, H.

"Specific," for (a target sequence), as used herein, refers broadly to a probe or primer hybridizes under standard stringent hybridization conditions only to the target sequence in a sample comprising the target sequence.

"Sequence identity," with regard to nucleotide sequences (DNA or RNA), as used herein, refers broadly to the number of positions with identical nucleotides divided by the number of nucleotides in the shorter of the two sequences. The alignment of the two nucleotide sequences is performed by the Wilbur and Lipmann algorithm (Wilbur and Lipmann, 1983, Proc. Nat. Acad. Sci. USA 80:726) using a window-size of 20 nucleotides, a word length of 4 nucleotides, and a gap penalty of 4. Computer-assisted analysis and interpretation of sequence data, including sequence alignment as described above, can, e.g., be conveniently performed using the sequence analysis software package of the Genetics Computer Group (GCG, University of Wisconsin Biotechnology center).

"Solid support," "support," and "substrate," as used herein, refers broadly to any material that provides a solid or semi-solid structure with which another material can be attached.

"Variant," as used herein, refers broadly to means a nucleotide sequence that codes for the amino acid sequence differs from the base sequence from which it is derived in that one or more amino acids within the encoded sequence are substituted for other amino acids.

Event

An "event" is a genetic locus that, as a result of genetic engineering, carries a transgene of interest. An "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. An "event" refers to the original transformant and progeny of the transformant that includes the heterologous DNA. An "event" also refers to progeny produced by a sexual outcross between the transformant and another event that include the heterologous DNA. Even after repeated back-crossing to a recurrent parent, the inserted DNA and flanking genomic DNA from the transformed parent is present in the progeny of the cross at the same chromosomal location. An "event" also refers to DNA from the original transformant comprising the inserted DNA and flanking genomic sequence immediately adjacent to the inserted DNA, that would be expected to be transferred to a progeny that receives the inserted DNA including the transgene of interest as the result of a sexual cross of one parental line that includes the inserted DNA (e.g., the original transformant and progeny resulting from selfing) and a parental line that does not contain the inserted DNA.

The transformation of a plant with heterologous DNA, or by back-crossing with plants obtained by such transformation, typically results in a population of transformants comprising a multitude of separate events. Individual events from this group of events are selected based on various criteria such as expression and stability of the transgene(s) and its compatibility with optimal agronomic characteristics of the plant comprising it. As described herein, event Pp009-401, event Pp009-415, and event Pp009-469 were selected based on such characteristics including glyphosate tolerance and enhanced turfgrass quality.

The heterologous (or foreign) DNA can be characterized by the particular location in which it is incorporated into the plant genome. The foreign DNA can be detected by identifying regions or sequences that flank the foreign DNA. These flanking/junction regions or sequences are different from the introduced DNA, and are preferably DNA from the plant genome which is located either immediately upstream of and contiguous with, or immediately downstream of and contiguous with the foreign DNA.

Events Pp009-401, Pp009-415, and Pp009-469

The invention relates to Kentucky bluegrass transgenic events designated Pp009-401, Pp009-415, and Pp009-469, and plants, cells, plant parts, and seeds comprising these events. The events involve the transformation of two expression cassettes depicted in FIG. 1. The first cassette includes a 5-enol-pyruvylshikimate-3-phosphate synthase (EPSPS) gene from *Arabidopsis*, and the second cassette includes a gibberellic acid 2-oxidase gene from spinach. Plants comprising these events are glyphosate tolerant and possess enhanced turfgrass qualities (e.g., require less mowing, have a darker green color, and generate a thicker, fuller stand). The events described herein may be in the original transformant and progeny of the transformant that include the heterologous DNA.

Plants comprising Pp009-401, Pp009-415, or Pp009-469 may be produced by growing seeds comprising these events. For example, plants may be grown from seeds comprising events Pp009-401, Pp009-415, and Pp009-469 having been deposited with American Type Culture Collection (ATCC) as Accession Nos. PTA-120354, PTA-120353, and PTA-120355, respectively. Plants comprising the events may also be obtained by propagation of and/or breeding of plants comprising the events (e.g., a plant grown from a seed deposited with the ATCC). Plant parts, such as bulb, tuber, crown, stem, tiller, cuttings including un-rooted cuttings, rooted cuttings, and callus cuttings or callus-generated plantlets; apical meristems, pollen, ovule, flowers, shoots, stolons, progagules, seeds, runners, corms, rhizomes, roots, or leaves may that comprise events Pp009-401, Pp009-415 or Pp009-469 are also encompassed herein.

Progeny comprising the events may be produced by a sexual outcross between a parental plant comprising Pp009-401, Pp009-415, or Pp009-469 (e.g., original transformant, plant grown from seed comprising event), and itself or another parental plant that lacks Pp009-401, Pp009-415, or Pp009-469, respectively. The other plant may also lack glyphosate tolerance. The other plant may, however, comprise other events and/or desirable characteristics.

In one embodiment, the invention provides for a method of producing a turfgrass (e.g., Kentucky bluegrass) plant or seed comprising crossing a Kentucky bluegrass plant comprising event Pp009-401, event Pp009-415, or event Pp009-469 with a plant lacking event Pp009-401, event Pp009-415, or event Pp009-469 (or by selfing with a plant comprising event Pp009-401, event Pp009-415, or event Pp009-469), and planting seed obtained from the cross or selfing, wherein the seed comprises event Pp009-401, event Pp009-415, or event Pp009-469. The plant lacking the event can be a Kentucky bluegrass (*Poa pratensis* L.) plant or other plant species that can breed with Kentucky blue grass (e.g., *P. interior, P. arachnifera*). The method may also involve selecting progeny plants tolerant to glyphosate. The method may further include backcrossing (or selfing) the progeny plants with a Kentucky bluegrass plant comprising event Pp009-401, event Pp009-415, or event Pp009-469. The backcrossing or selfing step may be performed more than once. Plants and seeds (comprising event Pp009-401, event Pp009-415, or event Pp009-469) obtained from any of these methods are encompassed herein.

In another embodiment, a glyphosate tolerant, enhanced turfgrass quality Kentucky bluegrass plant can be bred by first sexually crossing a parental Kentucky bluegrass plant, or other sexually compatible Kentucky bluegrass plant, grown from the transgenic Kentucky bluegrass plant derived from transformation with the plant expression cassettes contained in pSCO761 (FIG. 1) that tolerates application of glyphosate herbicide, and a second parental Kentucky bluegrass plant that lacks the tolerance to glyphosate herbicide, thereby producing a plurality of first progeny plants; and then selecting a first progeny plant that is tolerant to application of glyphosate herbicide (i.e., first glyphosate herbicide tolerant plant); and selfing or crossing the first progeny plant, thereby producing a plurality of second progeny plants; and then selecting from the second progeny plants, a glyphosate herbicide tolerant plant (i.e., second glyphosate herbicide tolerant plant). These steps can further include the back-crossing or crossing of the first glyphosate tolerant progeny plant or the second glyphosate tolerant progeny plant to the second parental Kentucky bluegrass plant or sexually compatible species or a third parental Kentucky bluegrass plant or sexually compatible species, thereby producing a Kentucky bluegrass plant that tolerates the application of glyphosate herbicide. Plants and seeds (comprising events Pp009-401, event Pp009-415, or event Pp009-469) obtained from any of these methods are encompassed herein.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references (e.g., Fehr, in Breeding Methods for Cultivar Development, Wilcox J. ed., American Society of Agronomy, Madison Wis. (1987)).

EPSPS Variant Nucleic Acid

The nucleic acid comprising SEQ ID NO: 12 is a cDNA and encodes a variant of the enzyme 5-enolpyruvyl-3-phosphoshikimate synthase (EPSPS):

```
                                      (SEQ ID NO: 12)
CCCAGGTGTCCCGCATCTGCAACGGCGTGCAGAACCCATCCCTCATCTCC

AACCTCTCCAAGTCCTCCCAGCGCAAGTCCCCACTCTCCGTGTCCCTCAA

GACCCAGCAACACCCACGCGCCTACCCAATCTCCAGCTCCTGGGGCCTCA

AGAAGTCCGGCATGACCCTCATCGGCTCCGAGCTGCGCCCACTCAAGGTG

ATGTCCTCCGTGTCCACCGCCGAGAAGGCCTCCGAGATCGTGCTCCAGCC
```

-continued

AATCCGCGAGATTTCCGGCCTCATCAAGCTCCCAGGCTCCAAGTCCCTCT

CCAACCGCATCCTCCTGCTCGCCGCTCTCTCCGAGGGCACCACCGTGGTG

GACAACCTGCTCAACTCCGACGACATCAACTACATGCTCGACGCCCTCAA

GCGCCTCGGCCTCAACGTGGAGACCGACTCCGAGAACAACCGCGCCGTGG

TGGAGGGCTGCGGCGGCATCTTCCCAGCCTCCATCGATTCCAAGTCCGAC

ATCGAGCTGTACCTCGGCAACTCCGGCACCTGCATGAGGTCACTCACGGC

GGCGGTCACCGCGGCTGGCGGCAACGCCTCCTACGTGCTCGACGGCGTGC

CAAGGATGCGCGAGCGCCCAATCGGCGACCTCGTGGTGGGCCTCAAGCAA

CTCGGCGCCGACGTGGAGTGCACCCTCGGCACCAACTGCCCACCAGTGCG

CGTGAACGCCAACGGCGGCCTCCCAGGCGGCAAGGTGAAGCTCTCCGGCT

CCATCTCCTCCCAGTACCTCACCGCCCTGCTCATGTCCGCCCCACTCGCC

CTCGGCGACGTGGAGATCGAGATCGTGGACAAGCTCATCTCCGTGCCATA

CGTGGAGATGACCCTCAAGCTCATGGAGCGCTTCGGCGTGTCCGTGGAGC

ACTCCGACAGCTGGGACCGCTTCTTCGTGAAGGGCGGCCAGAAGTACAAG

TCCCCAGGCAACGCCTACGTGGAGGGCGACGCCTCCTCCGCCTCCTACTT

CCTCGCTGGCGCTGCCATCACCGGCGAGACCGTGACCGTGGAGGGGTGCG

GCACCACCAGCCTCCAAGGCGACGTGAAGTTCGCCGAGGTGCTCGAGAAG

ATGGGCTGCAAGGTGTCCTGGACCGAGAACTCCGTGACCGTGACCGGCCC

ACCAAGGGACGCCTTCGGCATGAGGCACCTCCGCGCCATCGACGTGAACA

TGAACAAGATGCCAGACGTGGCCATGACCCTCGCCGTGGTGGCCCTCTTC

GCCGACGGCCCAACCACCATCAGGGACGTGGCCAGCTGGCGCGTGAAGGA

GACCGAGCGCATGATCGCCATCTGCACCGAGCTGAGAAAGCTCGGCGCCA

CCGTCGAGGAGGGCTCCGACTACTGCGTGATCACCCCACCAAAGAAGGTC

AAGACCGCCGAGATCGACACCTACGACGACCACCGCATGGCGATGGCCTT

CTCCCTCGCCGCCTGCGCCGACGTGCCGATCACCATCAACGACCCAGGCT

GCACCCGCAAGACCTTCCCAGACTACTTCCAGGTGCTCGAGCGCATCACC

AAGCACT

This EPSPS variant has a lower affinity for glyphosate and thus can retain catalytic activity in the presence of glyphosate. The first cassette is a nucleic acid comprising SEQ ID NO: 10 is a transgene expression cassette comprising the variant EPSPS (SEQ ID NO: 12) that confers glyphosate resistance and enhanced turfgrass characteristics. The first cassette includes the rice ubiquitin promoter (P-Os.UBQ, also referred to as P-rUBQ) and rice actin 1 intron (I-Os. Act1, also referred to as ract intron), operably connected to a glyphosate tolerant 5-enol-pyruvylshikimate-3-phosphate synthase (EPSPS) variant and operably connected to a *Zea mays* alcohol dehydrogenase transcriptional terminator.

Gibberellic Acid 2-Oxidase (GA2OX) Nucleic Acid

The nucleic acid comprising SEQ ID NO: 13 is a cDNA and encodes gibberellic acid 2-oxidase (GA2OX):

(SEQ ID NO: 13)

ATGGCCTCCACCAAGGTGGTCGAGCACCTCAAGGAGAACGTCCTCTGGAA

GCAGGCCATCATGGACCGCAACGCCAACATCTCCGACCCACCGTTCGAGG

-continued

AGACCTACAAGAACCTCCTGCTCAAGCACAACATCACCCCGCTCACCACC

ACCACGACCACGACGACCACCACGGCGACCATCGAGGTGAGGGATCTCCC

ACTCATCGACCTCTCCAGGCTCGTGGCCACCGCCGCCAAGGAGCGCGAGA

ACTGCAAGAGGGATATCGCCAACGCCTCCCGCGAGTGGGGCTTCTTCCAG

GTGGTGAACCACGGCATCCCGCATAGGATGCTCGAGGAGATGAACAAGGA

GCAGGTCAAGGTGTTCCGCGAGCCGTTCAACAAGAAGAAGGGCGACAACT

GCATGAACCTCAGGCTCTCCCCAGGCTCCTACAGGTGGGGCTCCCCGACC

CCGAACTGCCTCTCCCAGCTCTCCTGGTCCGAGGCCTTCCACATCCCGAT

GAACGACATCTGCTCCAACGCCCCGAGGAACATTGCCAACGGCAACCCGA

ACATCTCCAACCTCTGCTCCACCGTGAAGCAGTTCGCCACCACCGTGTCC

GAGCTGGCCAACAAGCTCGCCAACATCCTCGTCGAGAAGCTCGGCCATGA

CGAGCTGACCTTCATCGAGGAGAAGTGCTCCCCGAACACGTGCTACCTCA

GGATGAACCGCTACCCGCCGTGCCCAAAGTACTCCCACGTGCTCGGCCTC

ATGCCACATACCGACTCCGACTTCCTCACCATCCTCTACCAGGACCAGGT

GGGCGGCCTCCAGCTCGTGAAGGACGGCCGCTGGATTTCCGTGAAGCCGA

ACCCAGAGGCCCTCATCGTGAACATCGGCGACCTCTTCCAGGCCTGGTCT

AACGGCGTGTACAAGTCCGTGGTGCATAGGGTGGTGGCCAACCCGAGGTT

CGAGAGGTTCTCTACCGCCTACTTCCTCTGCCCGTCCGGCGACGCCGTGA

TCCAGTCCTACCGCGAGCCGTCTATGTACCGCAAGTTCAGCTTCGGCGAG

TACAGGCAGCAGGTCCAGCAGGACGTGCGCGAGTTCGGCCACAAGATCGG

CCTCTCCCGCTTCCTCATCTGCAAC

The second transgene expression cassette is a nucleic acid construct that comprises the Os.GOS2 promoter, operably connected to gibberellic acid 2-oxidase and operably connected to a *Solanum pennellii* histone H1 gene transcriptional terminator. Expression of this nucleic acid leads to enhanced turfgrass quality in grasses.

Kentucky Bluegrass Comprising Variant EPSPS or GA2OX and Variant EPSPS Transgenes The invention provides Kentucky bluegrass comprising the nucleic acid sequences of SEQ ID NO: 10, SEQ ID NO: 11, SEQ ID NO: 12, and/or SEQ ID NO: 13. The Kentucky bluegrass may be transformed with the two expression cassettes depicted in FIGS. 9 and 10. The first cassette includes a variant 5-enol-pyruvylshikimate-3-phosphate synthase (EPSPS) variant from *Arabidopsis* (SEQ ID NO: 9) [FIG. 9], and the second cassette includes a gibberellic acid 2-oxidase gene from spinach (SEQ ID NO: 10) [FIG. 10]. The sequences described herein may be in the original transformant and progeny of the transformant that include the heterologous DNA. The Kentucky bluegrass may be transformed with the nucleic acid sequence of SEQ ID NO: 12. The Kentucky bluegrass transformed with the nucleic acid of SEQ ID NO: 12 then may be transformed with the nucleic acid of SEQ ID NO: 13. The Kentucky bluegrass may comprise the nucleic acid sequence of SEQ ID NO: 12. The Kentucky bluegrass may comprise the nucleic acid sequence of SEQ ID NO: 12 and SEQ ID NO: 13. Plants comprising these sequences are glyphosate tolerant and possess enhanced turfgrass qualities (e.g., require less mowing, have a darker green color, and generate a thicker, fuller stand).

Kentucky bluegrass comprising the nucleic acid sequences of SEQ ID NO: 10, SEQ ID NO: 11, SEQ ID NO: 12, and/or SEQ ID NO: 13 may be produced by growing seeds comprising these nucleic acids. Kentucky bluegrass comprising the sequences may also be obtained by propagation of and/or breeding of Kentucky bluegrass comprising the sequences (e.g., a plant grown from a seed comprising the nucleic acid sequences of SEQ ID NO: 10, SEQ ID NO: 11, SEQ ID NO: 12, and/or SEQ ID NO: 13). Plant parts, such as bulb, tuber, crown, stem, tiller, cuttings including un-rooted cuttings, rooted cuttings, and callus cuttings or callus-generated plantlets; apical meristems, pollen, ovule, flowers, shoots, stolons, progagules, seeds, runners, corms, rhizomes, roots, or leaves that comprise the nucleic acid sequences of SEQ ID NO: 10, SEQ ID NO: 11, SEQ ID NO: 12, and/or SEQ ID NO: 13 are also encompassed herein.

Progeny comprising the sequences may be produced by a sexual outcross between a parental Kentucky bluegrass plant comprising the nucleic acid sequences of SEQ ID NO: 10, SEQ ID NO: 11, SEQ ID NO: 12, and/or SEQ ID NO: 13 (e.g., original transformant, plant grown from seed comprising the nucleic acid sequences of SEQ ID NO: 10, SEQ ID NO: 11, SEQ ID NO: 12, and/or SEQ ID NO: 13), and itself or another parental Kentucky bluegrass plant that lacks the nucleic acid sequences of SEQ ID NO: 10, SEQ ID NO: 11, SEQ ID NO: 12, and/or SEQ ID NO: 13, respectively. The other Kentucky bluegrass plant may also lack glyphosate tolerance. The other plant may, however, comprise other sequences, events, and/or desirable characteristics.

In one embodiment, the invention provides for a method of producing a turfgrass (e.g., Kentucky bluegrass) plant or seed comprising crossing a Kentucky bluegrass plant comprising the nucleic acid sequences of SEQ ID NO: 10, SEQ ID NO: 11, SEQ ID NO: 12, and/or SEQ ID NO: 13 with a plant lacking the nucleic acid sequences of SEQ ID NO: 10, SEQ ID NO: 11, SEQ ID NO: 12, and/or SEQ ID NO: 13, and planting seed obtained from the cross or selfing, wherein the seed comprises the nucleic acid sequences of SEQ ID NO: 10, SEQ ID NO: 11, SEQ ID NO: 12, and/or SEQ ID NO: 13. The plant lacking the sequences described herein can be a Kentucky bluegrass (*Poa pratensis* L.) plant or other plant species that can breed with Kentucky blue grass (e.g., *P. interior, P. arachnifera*). The method may also involve selecting progeny Kentucky bluegrass plants tolerant to glyphosate. The method may further include back-crossing (or selfing) the progeny plants with a Kentucky bluegrass plant comprising the nucleic acid sequences of SEQ ID NO: 10, SEQ ID NO: 11, SEQ ID NO: 12, and/or SEQ ID NO: 13. The backcrossing or selfing step may be performed more than once. Plants and seeds (comprising the nucleic acid sequences of SEQ ID NO: 10, SEQ ID NO: 11, SEQ ID NO: 12, and/or SEQ ID NO: 13) obtained from any of these methods are encompassed herein.

In another embodiment, a glyphosate tolerant, enhanced turfgrass quality Kentucky bluegrass plant can be bred by first sexually crossing a parental Kentucky bluegrass plant, or other sexually compatible Kentucky bluegrass plant, grown from the transgenic Kentucky bluegrass plant derived from transformation with the plant expression cassettes contained in the pSCO761 plasmid (FIG. 1) that tolerates application of glyphosate herbicide, and a second parental Kentucky bluegrass plant that lacks the tolerance to glyphosate herbicide, thereby producing a plurality of first progeny plants; and then selecting a first progeny plant that is tolerant to application of glyphosate herbicide (i.e., first glyphosate herbicide tolerant plant); and selfing or crossing the first progeny plant, thereby producing a plurality of second progeny plants; and then selecting from the second progeny plants, a glyphosate herbicide tolerant plant (i.e., second glyphosate herbicide tolerant plant). These steps can further include the back-crossing or crossing of the first glyphosate tolerant progeny plant or the second glyphosate tolerant progeny plant to the second parental Kentucky bluegrass plant or sexually compatible species or a third parental Kentucky bluegrass plant or sexually compatible species, thereby producing a Kentucky bluegrass plant that tolerates the application of glyphosate herbicide. Plants and seeds (comprising the nucleic acid sequences of SEQ ID NO: 10, SEQ ID NO: 11, SEQ ID NO: 12, and/or SEQ ID NO: 13) obtained from any of these methods are encompassed herein.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references (e.g., Fehr, in Breeding Methods for Cultivar Development, Wilcox J. ed., American Society of Agronomy, Madison Wis. (1987)).

Grasses Comprising EPSPS or GA2OX and Variant EPSPS Transgenes

The invention provides grasses comprising the nucleic acid sequences of SEQ ID NO: 10, SEQ ID NO: 11, SEQ ID NO: 12, and/or SEQ ID NO: 13. Grasses may be transformed with the two expression cassettes depicted in FIGS. 9 and 10. The first cassette includes a variant 5-enolpyruvylshikimate-3-phosphate synthase (EPSPS) gene from *Arabidopsis* (SEQ ID NO: 9) [FIG. 9], and the second cassette includes a gibberellic acid 2-oxidase gene from spinach (SEQ ID NO: 10) [FIG. 10]. Grasses comprising these sequences are glyphosate tolerant and possess enhanced turfgrass qualities (e.g., require less mowing, have a darker green color, and generate a thicker, fuller stand). The grass may be transformed with the nucleic acid sequence of SEQ ID NO: 12. The grass transformed with the nucleic acid of SEQ ID NO: 12 then may be transformed with the nucleic acid of SEQ ID NO: 13. The grass may comprise the nucleic acid sequence of SEQ ID NO: 12. The grass may comprise the nucleic acid sequence of SEQ ID NO: 12 and SEQ ID NO: 13. The sequences described herein may be in the original transformant and progeny of the transformant that include the heterologous DNA.

Grasses comprising the nucleic acid sequences of SEQ ID NO: 10, SEQ ID NO: 11, SEQ ID NO: 12, and/or SEQ ID NO: 13 may be produced by growing seeds comprising these nucleic acids. Grasses comprising the sequences may also be obtained by propagation of and/or breeding of grasses comprising the sequences (e.g., a grass grown from a seed comprising the nucleic acid sequences of SEQ ID NO: 10, SEQ ID NO: 11, SEQ ID NO: 12, and/or SEQ ID NO: 13). Grass parts, such as bulb, stem, tiller, cuttings including un-rooted cuttings, rooted cuttings, and callus cuttings or callus-generated plantlets; apical meristems, pollen, ovule, flowers, shoots, stolons, progagules, seeds, runners, rhizomes, roots, or leaves, that comprise the nucleic acid sequences of SEQ ID NO: 10, SEQ ID NO: 11, SEQ ID NO: 12, and/or SEQ ID NO: 13 are also encompassed herein.

Progeny comprising the sequences may be produced by a sexual outcross between a parental grass comprising the nucleic acid sequences of SEQ ID NO: 10, SEQ ID NO: 11, SEQ ID NO: 12, and/or SEQ ID NO: 13 (e.g., original transformant, grass grown from seed comprising the nucleic acid sequences of SEQ ID NO: 10, SEQ ID NO: 11, SEQ ID NO: 12, and/or SEQ ID NO: 13), and itself or another parental plant that lacks the nucleic acid sequences of SEQ ID NO: 10, SEQ ID NO: 11, SEQ ID NO: 12, and/or SEQ ID NO: 13, respectively. The other grass may also lack glyphosate tolerance. The other grass may, however, comprise other sequences, events, and/or desirable characteristics.

In one embodiment, the invention provides for a method of producing a grass (e.g., Kentucky bluegrass) plant or seed comprising crossing a grass comprising the nucleic acid sequences of SEQ ID NO: 10, SEQ ID NO: 11, SEQ ID NO: 12, and/or SEQ ID NO: 13 with a grass lacking the nucleic acid sequences of SEQ ID NO: 10, SEQ ID NO: 11, SEQ ID NO: 12, and/or SEQ ID NO: 13, and planting seed obtained from the cross or selfing, wherein the seed comprises the nucleic acid sequences of SEQ ID NO: 10, SEQ ID NO: 11, SEQ ID NO: 12, and/or SEQ ID NO: 13. The grass lacking the sequences described herein can be a Kentucky bluegrass (*Poa pratensis* L.) plant or other plant species that can breed with Kentucky blue grass (e.g., *P. interior, P. arachnifera*). The grass transformed with the expression cassettes depicted in FIG. 9 may be Bahia grass, bent grass, Bermuda grass, Blue grama grass, Buffalo grass, centipedes grasses, fescue grass, optionally needle-leaved Fescue grass or broad-leaved Fescue grass, Kentucky bluegrass, rygrass optionally annual ryegrass or perennial reygrass, seashore *paspalum*, St. Augustine grass, or *Zoysia* grass.

The method may also involve selecting progeny grass tolerant to glyphosate. The method may further include backcrossing (or selfing) the progeny grass with a grass plant comprising the nucleic acid sequences of SEQ ID NO: 10, SEQ ID NO: 11, SEQ ID NO: 12, and/or SEQ ID NO: 13. The backcrossing or selfing step may be performed more than once. Grass plants and seeds (comprising the nucleic acid sequences of SEQ ID NO: 10, SEQ ID NO: 11, SEQ ID NO: 12, and/or SEQ ID NO: 13) obtained from any of these methods are encompassed herein.

In another embodiment, a glyphosate tolerant, enhanced grass can be bred by first sexually crossing a parental grass, or other sexually compatible grass, grown from the transgenic grass derived from transformation with the plant expression cassettes contained in the pSCO761 plasmid (FIG. 1) that tolerates application of glyphosate herbicide, and a second parental grass that lacks the tolerance to glyphosate herbicide, thereby producing a plurality of first progeny grasses; and then selecting a first progeny grass that is tolerant to application of glyphosate herbicide (i.e., first glyphosate herbicide tolerant plant); and selfing or crossing the first progeny grass, thereby producing a plurality of second progeny grasses; and then selecting from the second progeny grasses, a glyphosate herbicide tolerant grass (i.e., second glyphosate herbicide tolerant grass). These steps can further include the back-crossing or crossing of the first glyphosate tolerant progeny grass or the second glyphosate tolerant progeny grass to the second parental grass or sexually compatible species or a third parental grass or sexually compatible species, thereby producing a grass that tolerates the application of glyphosate herbicide. Grasses and seeds (comprising the nucleic acid sequences of SEQ ID NO: 10, SEQ ID NO: 11, SEQ ID NO: 12, and/or SEQ ID NO: 13) obtained from any of these methods are encompassed herein.

It is also to be understood that two different transgenic grasses can also be mated to produce offspring that contain two independently segregating added, exogenous genes. Selfing of appropriate progeny can produce grasses that are homozygous for both added, exogenous genes. Back-crossing to a parental grass and out-crossing with a non-transgenic grass are also contemplated, as is vegetative propagation. Descriptions of other breeding methods that are commonly used for different traits and crops can be found in one of several references (e.g., Fehr, in Breeding Methods for Cultivar Development, Wilcox J. ed., American Society of Agronomy, Madison Wis. (1987)).

Plants Comprising Variant EPSPS or GA2OX Transgene and Variant EPSPS

The invention provides to plants comprising the nucleic acid sequences of SEQ ID NO: 10, SEQ ID NO: 11, SEQ ID NO: 12, and/or SEQ ID NO: 13. Plants may be transformed with the two expression cassettes depicted in FIGS. 9 and 10. The first cassette includes a variant 5-enol-pyruvylshikimate-3-phosphate synthase (EPSPS) gene from *Arabidopsis* (SEQ ID NO: 9) [FIG. 9], and the second cassette includes a gibberellic acid 2-oxidase gene from spinach (SEQ ID NO: 10) [FIG. 10]. The plants may comprise the EPSPS gene comprising the sequence of SEQ ID NO: 12. Plants comprising the EPSPS sequence are glyphosate tolerant. The plants may be transformed with the nucleic acid sequence of SEQ ID NO: 12. The plants transformed with the nucleic acid of SEQ ID NO: 12 then may be transformed with the nucleic acid of SEQ ID NO: 13. The plants may comprise the nucleic acid sequence of SEQ ID NO: 12. The plants may comprise the nucleic acid sequence of SEQ ID NO: 12 and SEQ ID NO: 13. Plants comprising the variant GA2OX transgene may exhibit shorter stature, darker green color, thicker/more density, shorter stolons, better nutrient use efficiency, better water use efficiency. The sequences described herein may be in the original transformant and progeny of the transformant that include the heterologous DNA.

The invention provides for plants comprising the nucleic acid molecules comprising SEQ ID NO: 10, SEQ ID NO: 11, SEQ ID NO: 12, or SEQ ID NO: 13 including but not limited to flowers, vegetables, fruits, herbs, grass, trees, or perennial plant parts (e.g., bulb, tuber, crown, stem, tiller, cuttings including un-rooted cuttings, rooted cuttings, and callus cuttings or callus-generated plantlets; apical meristems, pollen, ovule, flowers, shoots, stolons, progagules, seeds, runners, corms, rhizomes, roots, leaves). Plant life that may comprise the nucleic acid molecules comprising SEQ ID NO: 10, SEQ ID NO: 11, SEQ ID NO: 12, or SEQ ID NO: 13 include but are not limited to plants, plant cuttings, young plants or seeds from ornamental plants including but not limited to geranium, *petunia, impatiens, verbena*, dahlia, pansy, *vinca, ipomoea, lantana, salvia*, snapdragon, scaevola, torenia, *lobelia*, dipladenia, calibrachoa, asters, agerantum, *phlox*, penstemon, gaillardia, *zinnia, coleus*, osteospermum, *gerbera, begonia*, angelonia, *dianthus*, calendula, *campanula, celosia, portulaca, viola*, mums; vegetables such as tomatoes, peppers, broccoli, cucumber, zucchini, raddish, eggplant, cabbage, lettuce, spinach, beet, carrots, spinach, squash, radish, beans, potato, onion; herbs such as basil, rosemary, dill, cilantro, coriander, thyme, oregano, mint; fruits such as, blueberry, blackberry, raspberry, watermelon, apple, cherry, pear, orange, lemon, and pumpkin; turfgrasses such as bluegrass, St. Augustinegrass, bermudagrass, bentgrass, bahiagrass, centipedegrass, tall fescue, buffalograss, zoysiagrass, ryegrass, fine fescue; and agricultural crops such as corn, sugar cane, wheat, soybean, tobacco, or citrus. Without being limited to varieties enumerated herein, the varieties of ornamental plants of the present invention comprising the nucleic acid molecules comprising SEQ ID NO: 10, SEQ ID NO: 11, SEQ ID NO: 12, or SEQ ID NO: 13 may be varieties of the *vinca* genus; plants of the cleome genus; plants of the *Helianthus annuus* genus; plants of the *Impatients hawkeri* genus; plants of the *lantana* genus; plants of the *Mandevilla hydrida* genus; plants of the *pelargonium* interspecific genus Calliope; plants of the *Pentas lanceolata* genus; plants of the *Petunia pendula* genus; plants of the *rudbeckia* genus, plants of the *Viola cornuta* genus; plants of the *Viola wittrockiana* genus; and plants of the *zinnia* genus.

The invention provides for plants comprising the nucleic acid molecules comprising the event Pp009-401, Pp009-415, or Pp009-469 including but not limited to flowers, vegetables, fruits, herbs, grass, trees, or perennial plant parts (e.g., bulb, tuber, crown, stem, tiller, cuttings including un-rooted cuttings, rooted cuttings, and callus cuttings or callus-generated plantlets; apical meristems, pollen, ovule, flowers, shoots, stolons, progagules, seeds, runners, corms, rhizomes, roots, or leaves). Plant life that may comprise the nucleic acid molecules comprising the event Pp009-401, Pp009-415, or Pp009-469 include but are not limited to plants, plant cuttings, young plants or seeds from ornamental plants including but not limited to geranium, *petunia, impatiens, verbena*, dahlia, pansy, *vinca, ipomoea, lantana, salvia*, snapdragon, scaevola, torenia, *lobelia*, dipladenia, calibrachoa, asters, agerantum, *phlox*, penstemon, gaillardia, *zinnia, coleus*, osteospermum, *gerbera, begonia*, angelonia, *dianthus*, calendula, *campanula, celosia, portulaca, viola*, mums; vegetables such as tomatoes, peppers, broccoli, cucumber, zucchini, raddish, eggplant, cabbage, lettuce, spinach, beet, carrots, spinach, squash, radish, beans, potato, onion; herbs such as basil, rosemary, dill, cilantro, coriander, thyme, oregano, mint; fruits such as, blueberry, blackberry, raspberry, watermelon, apple, cherry, pear, orange, lemon, and pumpkin; turfgrasses such as bluegrass, St. Augustinegrass, bermudagrass, bentgrass, bahiagrass, centipedegrass, tall fescue, buffalograss, zoysiagrass, ryegrass, fine fescue; and agricultural crops such as corn, sugar cane, wheat, soybean, tobacco, or citrus. Without being limited to varieties enumerated herein, the varieties of ornamental plants of the present invention comprising the nucleic acid molecules comprising the event Pp009-401, Pp009-415, or Pp009-469 may be varieties of the *vinca* genus, such as Cora Cascade Polka Dot, Cora Cascade peach blush, Cora Cascade apricot, Exp. Cora Cascade apricot, Exp. Cora Cascade blush splash, Exp. Cora Cascade shell pink, Exp. Cora Cascade strawberry, Cora Cascade cherry, Exp. Cora Cascade cherry, Cora Cascade magenta, Cora Cascade lilac, Exp. Cora Cascade violet, Exp. Nirvana Cascade white, Exp. Nirvana Cascade polka dot, Nirvana Cascade pink blush, Nirvana Cascade® pink splash, Nirvana Cascade® burgundy, or Nirvana Cascade lavender eye; plants of the cleome genus, such as Sparkler F1 blush, Sparkler F1 rose, Sparkler F1 white, Sparkler® lavender; plants of the *Helianthus annuus* genus, such as Exp. Yellow Dark Ct Indeterminant, or Exp. Yellow Dark Ct Indeterminant; plants of the *Impatients hawkeri* genus Exp. NGI red, Exp. NGI red, Divine scarlet red, Exp. NGI orange, Divine orange bronze leaf, Exp. NGI salmon, Exp. New Guinea *Impatiens* salmon, Exp. New Guinea *Impatiens* salmon, Exp. NGI bicolor orange, Exp. NGI white, Exp. NGI white, Exp. New Guinea *Impatiens* pink, Divine pink, Exp. NGI violet, Divine violet, Exp. NGI lavender, or Divine lavender; plants of the *lantana* genus, such as Exp. Bandana white, Bandana® primrose, Bandana® peach, Bandana® rose upgrade, Exp. Bandana red, Exp. Bandana cherry, Bandana® orange sunrise, Bandana® trailing gold, or Exp. Bandana trailing red; plants of the *Mandevilla hydrida* genus Exp. Rio dark pink, Rio pink, Exp. Rio pink, Rio deep red, Exp. Rio red, or Exp. Rio white; plants of the *pelargonium* interspecific genus Calliope exp. It pk, Calliope exp. Coral (bicolor), Exp. Calliope hot rose, Exp. Calliope rose splash, Exp. Calliope burgundy, Calliope exp. lav, Exp. Calliope lavender rose, Calliope exp. ro, Calliope exp. Scarlet, Calliope Scarlet Fire "Cope Scarfir", Exp. Calliope hot scarlet, Calliope Dark Red "Ameri Trared", Exp. Calliope burgundy, Exp. Calliope violet, Exp. Calliope burgundy, Calliope exp. ro w/Eye, Exp. Caliente® lavender rose, Caliente Pink "Cante Pinka", Caliente exp. Dp.Pk, Exp. Caliente® salmon, Caliente Coral "Cante Coras", Caliente Orange "Cante Oran", Caliente exp. Vio, Caliente exp. Vio, Caliente exp. ro sp, Exp. Caliente® rose coral, or Caliente exp. pkbl; plants of the *Pentas lanceolata* genus, such as Exp. Trailing white, Exp. Trailing white, Exp. Trailing white, Exp. Trailing pink bicolor, Exp. Trailing pink bicolor, Exp. Trailing deep pink, Exp. Trailing rose, Exp. Trailing rose, Exp. Trailing cherry, or Exp. Trailing red; plants of the *Petunia pendula* genus, such as Plush white, Ramblin' white, Exp. Ramblin yellow, Plush red, Ramblin' red, Plush blue, or Ramblin' nu blue; plants of the *rudbeckia* genus, such as Tiger eye gold F1; plants of the *Tagetes erecta* genus, such as Perfection® yellow, Perfection® F1 gold, Perfection® F1 orange, Exp. Perfection Vanilla White, Asian Cut flower, Gold, Asian Cut flower, or Orange, plants of the *Viola cornuta* genus, such as Endurio yellow with violet wing, or Exp. Endurio yellow with violet wing; plants of the *Viola wittrockiana* genus, such as Exp Colossus Yellow/Blotch V1042, Mammoth Blue-ti-ful, Exp. WonderFall White, Exp. WonderFall Yellow, Exp. WonderFall Yellow Blotch, WonderdFall Yellow with Red Wing trailing, Exp. WonderFall Blue Blotch, WonderFall Blue Picotee Shades, Exp. WonderFall Purple; and plants of the *zinnia* genus, such as ZOWIE!YELLOW FLAME, Uproar® Rose, Uproar™ White 1695-1-T1, Uproar™ Deep Yellow 1695-17-T1, Uproar™ Orange 1695-8-T1, Uproar™ Scarlet 1695-10-T2.

The invention provides for the transformation of plants with any one of the nucleic acid sequence of SEQ ID NO: 10, 11, 12, or 13. The transformed plant comprising the nucleic acid sequence of SEQ ID NO: 9, 10, 11, 12, or 13 may be a grass, grain crop, crop, ornamental flower, legume, fruit, vegetable, herb, perennial plant, or tree.

The transformed plant comprising the nucleic acid sequence of SEQ ID NO: 9, 10, 11, 12, or 13 may be a root vegetable or vine vegetable.

The transformed grass comprising the nucleic acid sequence of SEQ ID NO: 9, 10, 11, 12, or 13 may be Bahia grass, bent grass, Bermuda grass, Blue grama grass, Buffalo grass, centipedes grasses, fescue grass, optionally needle-leaved Fescue grass, tall Fescue, or broad-leaved Fescue grass, Kentucky bluegrass, rygrass optionally annual ryegrass or perennial ryegrass, seashore *paspalum*, St. Augustine grass, or *Zoysia* grass.

The transformed grain crop comprising the nucleic acid sequence of SEQ ID NO: 9, 10, 11, 12, or 13 may be is barley, sorghum, millet, rice, canola, corn, oats, wheat, barley, or hops.

The transformed plant comprising the nucleic acid sequence of SEQ ID NO: 9, 10, 11, 12, or 13 may be soybean.

The transformed ornamental flower comprising the nucleic acid sequence of SEQ ID NO: 10, 11, 12, or 13 may be an annual or perennial ornamental flower. The ornamental flower may be a geranium, *petunia*, or daffodil.

The transformed legume comprising the nucleic acid sequence of SEQ ID NO: 10, 11, 12, or 13 may be alfalfa, clover, peas, beans, lentils, lupins, mesquite, carob, soybeans, peanuts, or tamarind.

The transformed fruit comprising the nucleic acid sequence of SEQ ID NO: 10, 11, 12, or 13 may be grape, raspberry, blueberry, strawberry, blackberry, watermelon, apple, cherry, pear, orange, lemon, or pumpkin.

The transformed vegetable comprising the nucleic acid sequence of SEQ ID NO: 10, 11, 12, or 13 may be asparagus, Brussels sprouts, cabbage, carrots, celery, chard, collard greens, endive, tomatoes, beans, peas, broccoli, cauliflower, bell pepper, eggplant, kale, lettuce, okra, onion, radish, spinach, peppers, broccoli, cucumber, zucchini, eggplant, beet, squash, beans, potato, or onion.

The transformed herb comprising the nucleic acid sequence of SEQ ID NO: 10, 11, 12, or 13 may be anise, basil, caraway, cilantro, chamomile, dill, fennel, lavender, lemon grass, marjoram, oregano, parsley, rosemary, sage, thyme, or mint.

The transformed root vegetable comprising the nucleic acid sequence of SEQ ID NO: 10, 11, 12, or 13 may be turnip, potato, carrot, or beet.

The transformed vine vegetable comprising the nucleic acid sequence of SEQ ID NO: 10, 11, 12, or 13 may be cucumber, pumpkins, squash, melon, or zucchini.

The transformed agricultural crop comprising the nucleic acid sequence of SEQ ID NO: 10, 11, 12, or 13 may be cotton, corn, sugar cane, wheat, soybean, tobacco, or citrus.

The transformed ornamental plant comprising the nucleic acid molecules comprising SEQ ID NO: 10, SEQ ID NO: 11, SEQ ID NO: 12, or SEQ ID NO: 13 include but not limited to geranium, *petunia, impatiens, verbena*, dahlia, pansy, *vinca, ipomoea, lantana, salvia*, snapdragon, scaevola, torenia, *lobelia*, dipladenia, calibrachoa, asters, agerantum, *phlox*, penstemon, gaillardia, *zinnia, coleus*, osteospermum, *gerbera, begonia*, angelonia, *dianthus*, calendula, *campanula, celosia, portulaca, viola*, or mums.

The varieties of ornamental plants of the present invention comprising the nucleic acid molecules comprising SEQ ID NO: 10, SEQ ID NO: 11, SEQ ID NO: 12, or SEQ ID NO: 13 may be varieties of the *vinca* genus; plants of the cleome genus; plants of the *Helianthus annuus* genus; plants of the *lantana* genus; plants of the *pelargonium* interspecific genus Calliope; plants of the *Pentas lanceolata* genus; plants of the *rudbeckia* genus, plants of the *Viola cornuta* genus; plants of the *Viola wittrockiana* genus; and plants of the *zinnia* genus.

The invention provides plants comprising the nucleic acid sequence of SEQ ID NO: 12 and plants, cells, plant parts, and seeds comprising this sequence. Plants comprising these sequences are glyphosate tolerant. The sequences described herein may be in the original transformant and progeny of the transformant that include the heterologous DNA. The plants transformed with the nucleic acid sequence of SEQ ID NO: 12 may be a grass, grain crop, crop, ornamental flower, legume, fruit bush, vegetable, root vegetable, herb, or a vine vegetable.

Plants comprising nucleic acid sequence of SEQ ID NO: 12 may be produced by growing seeds comprising these nucleic acids. Plants comprising the sequences may also be obtained by propagation of and/or breeding of plants comprising the sequences (e.g., a plant grown from a seed comprising nucleic acid sequence of SEQ ID NO: 12). Plant parts, such as bulb, tuber, crown, stem, tiller, cuttings including un-rooted cuttings, rooted cuttings, and callus cuttings or callus-generated plantlets; apical meristems, pollen, ovule, flowers, shoots, stolons, progagules, seeds, runners, corms, rhizomes, roots, or leaves, that comprise nucleic acid sequence of SEQ ID NO: 12 are also encompassed herein.

Progeny comprising the sequences may be produced by a sexual outcross between a parental plant comprising nucleic acid sequence of SEQ ID NO: 12 (e.g., original transformant, plant grown from seed comprising nucleic acid sequence of SEQ ID NO: 12), and itself or another parental plant that lacks nucleic acid sequence of SEQ ID NO: 12, respectively. The other plant may also lack glyphosate tolerance. The other plant may, however, comprise other events and/or desirable characteristics.

In one embodiment, the invention provides for a method of producing a plant or seed comprising crossing a plant comprising the nucleic acid sequence of SEQ ID NO: 12 with a plant lacking the nucleic acid sequences of SEQ ID NO: 12, and planting seed obtained from the cross or selfing, wherein the seed comprises the nucleic acid sequence of SEQ ID NO: 12. The plant lacking the sequences can be a plant species. The method may also involve selecting progeny plants tolerant to glyphosate. The method may further include backcrossing (or selfing) the progeny plants with a plant comprising the nucleic acid sequence of SEQ ID NO: 12. The backcrossing or selfing step may be performed more than once. Plants and seeds (comprising the nucleic acid sequence of SEQ ID NO: 12) obtained from any of these methods are encompassed herein.

In another embodiment, a glyphosate tolerant, plant can be bred by first sexually crossing a parental plant, or other sexually compatible plant, grown from the transgenic plant derived from transformation with the plant expression cassettes contained in the pSCO761 plasmid (FIG. 1) that tolerates application of glyphosate herbicide, and a second parental plant that lacks the tolerance to glyphosate herbicide, thereby producing a plurality of first progeny plants; and then selecting a first progeny plant that is tolerant to application of glyphosate herbicide (i.e., first glyphosate herbicide tolerant plant); and selfing or crossing the first progeny plant, thereby producing a plurality of second progeny plants; and then selecting from the second progeny plants, a glyphosate herbicide tolerant plant (i.e., second glyphosate herbicide tolerant plant). These steps can further include the back-crossing or crossing of the first glyphosate tolerant progeny plant or the second glyphosate tolerant progeny plant to the second parental plant or sexually compatible species or a third parental plant or sexually compatible species, thereby producing a plant that tolerates the application of glyphosate herbicide. Plants and seeds (comprising the nucleic acid sequences of SEQ ID NO: 12) obtained from any of these methods are encompassed herein.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references (e.g., Fehr, in Breeding Methods for Cultivar Development, Wilcox J. ed., American Society of Agronomy, Madison Wis. (1987)).

Plant Cells Comprising Elite Events

DNA molecules comprising event Pp009-401, event Pp009-415, or event Pp009-469 are provided herein. In a particular embodiment, the invention provides for DNA molecules comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, or complements thereof, or combinations thereof. Plants, plant cells, plant parts, and seeds comprising this DNA is also encompassed herein.

Nucleic acid molecules comprising the junction regions for event Pp009-401, event Pp009-415, or event Pp009-469 are also provided herein. In a particular embodiment, the invention provides for nucleic acid molecules comprising SEQ ID NO: 2, SEQ ID NO: 4, SEQ ID NO: 6, or complements thereof. Plants, plant cells, plant parts, and seeds comprising these nucleic acid molecules are also encompassed herein.

Nucleic acid molecules comprising the nucleotide sequences of SEQ ID NO: 10, 11, 12, and 13 are provided herein. In one embodiment, the invention provides for nucleic acid molecules comprising SEQ ID NO: 10, SEQ ID NO: 11, SEQ ID NO: 12, SEQ ID NO: 13, or complements thereof. Plants, plant cells, plant parts, and seeds comprising these nucleic acid molecules are also encompassed herein.

Primers and Probes

Primers and probes useful in the detection of event Pp009-401, event Pp009-415, and/or event Pp009-469, and methods of detecting these events are provided herein.

Primers and probes useful in the detection of nucleic acid molecules comprising SEQ ID NO: 10, SEQ ID NO: 11, SEQ ID NO: 12, SEQ ID NO: 13, and methods of detecting these events are provided herein.

A "primer" is a nucleic acid capable of priming the synthesis of a nascent nucleic acid in a template-dependent process, such as polymerase chain reaction (PCR). A primer anneals to a complementary target DNA strand by nucleic acid hybridization to form a hybrid between the primer and the target DNA strand, and is then extended along the target DNA strand by a polymerase, e.g., a DNA polymerase. Typically, primers are oligonucleotides from 10 to 30 nucleotides (e.g., 11, 12, 13, 14, 15, 16, 17, 18, 19, 20, 21, 22, 23, 24, 25, 26, 27, 28, or 29 nucleotides), but longer sequences may be employed. A "probe" can be used as a primer, but is designed to bind to target DNA or RNA and need not be used in an amplification reaction. Probes, like primers, may range from 10 to 30 nucleotides (e.g., 11, 12, 13, 14, 15, 16, 17, 18, 19, 20, 21, 22, 23, 24, 25, 26, 27, 28, or 29 nucleotides), but longer sequences may be employed.

Primers and probes are selected to be of sufficient length to specifically hybridize to a target sequence under stringent conditions. Preferably, the probes and primers have complete sequence similarity or complementarity with the target sequence, although primers and probes differing from the target sequence (e.g., by 1, 2, 3, 4, 5, 6, 7, 8, 9, or 10 mismatches) that retain the ability to hybridize to target sequences are encompassed herein.

Regarding the amplification of a target nucleic acid sequence (e.g. by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction. Specificity may be determined by the presence of positive and negative controls. For example, an analysis for event Pp009-401, Pp009-415 or Pp009-469 plant tissue sample may include a positive tissue control from event Pp009-401, Pp009-415 or Pp009-469, respectively, a negative control from a Kentucky bluegrass plant that is not event Pp009-401, Pp009-415 or Pp009-469, respectively, and a negative control that contains no Kentucky bluegrass DNA. In another example, when performing a PCR to identify the presence of event Pp009-401, event Pp009-415, or event Pp009-469, in unknown samples, a control is included of a set of primers with which a fragment within a "housekeeping gene" of the plant species of the event can be amplified. Housekeeping genes are genes expressed in most cell types and that are concerned with basic metabolic activities common to all cells. Preferably, the fragment amplified from the housekeeping gene is a fragment larger than the amplified integration fragment. Depending on the samples to be analyzed, other controls can be included.

Regarding the amplification of a target nucleic acid sequence (e.g. by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction. Specificity may be determined by the presence of positive and negative controls. For example, an analysis for plant tissue sample comprising nucleic acid molecules comprising SEQ ID NO: 10, SEQ ID NO: 11, SEQ ID NO: 12, or SEQ ID NO: 13 may include a positive tissue control from nucleic acid molecules comprising SEQ ID NO: 10, SEQ ID NO: 11, SEQ ID NO: 12, SEQ ID NO: 13, respectively, a negative control from a plant that is does not comprise nucleic acid molecules comprising SEQ ID NO: 10, SEQ ID NO: 11, SEQ ID NO: 12, SEQ ID NO: 13, respectively, and a negative control that contains none of the plant DNA. In another example, when performing a PCR to identify the presence of nucleic acid molecules comprising SEQ ID NO: 10, SEQ ID NO: 11, SEQ ID NO: 12, SEQ ID NO: 13, in unknown samples, a control is included of a set of primers with which a fragment within a "housekeeping gene" of the plant species of the event can be amplified. Housekeeping genes are genes expressed in most cell types and that are concerned with basic metabolic activities common to all cells. Preferably, the fragment amplified from the housekeeping gene is a fragment larger than the amplified integration fragment. Depending on the samples to be analyzed, other controls can be included.

Regarding the hybridization of a target sequence and a probe, the probe will specifically hybridize to the complement of the target nucleic acid sequence under standard stringency conditions. Standard stringency conditions as used herein refers to the conditions for hybridization described herein or to the conventional hybridizing conditions as described by Sambrook, et al. (2001) Molecular Cloning: A Laboratory Manual, Third Edition, Cold Spring Harbor Laboratory Press, NY, which for instance can comprise the following steps: (1) immobilizing plant genomic DNA fragments on a filter, (2) prehybridizing the filter for 1 to 2 hours at 42° C. in 50% formamide, 5×SSPE, 2×Denhardt's reagent and 0.1% SDS, or for 1 to 2 hours at 68° C. in 6×SSC, 2×Denhardt's reagent and 0.1% SDS, (3) adding the hybridization probe which has been labeled, (4) incubating for 16 to 24 hours, (5) washing the filter for 20 minutes at room temperature in 1×SSC, 0.1% SDS, (6) washing the filter three times for 20 minutes each at 68° C. in 0.2×SSC, 0.1% SDS, and (7) exposing the filter for 24 to 48 hours to X-ray film at −70° C. with an intensifying screen.

Contacting nucleic acid of a biological sample, with the probe, under conditions which allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of event Pp009-401, Pp009-415 or Pp009-469. The formation of this hybrid can be detected (e.g. labeling of the nucleic acid or probe), whereby the formation of this hybrid indicates the presence of nucleic acid molecules comprising SEQ ID NO: 10, SEQ ID NO: 11, SEQ ID NO: 12, SEQ ID NO: 13. Such identification methods based on hybridization with a specific probe (either on a solid phase carrier or in solution) have been described in the art. The target nucleic acid target or the probe may be labeled with a conventional detectable label or reporter molecule, e.g., a florescent molecule, a radioactive isotope, ligand, chemifluorescent, chemiluminescent agent, or enzyme.

Techniques for the manipulation of nucleic acids, such as, for example, for generating mutations in sequences, subcloning, labeling probes, sequencing, hybridization are well described in the scientific and patent literature. See, e.g., Sambrook, et al. (2001) (Eds.) *Molecular Cloning: A Laboratory Manual* ($3^{rd}$ Ed.) Cold Spring Harbor Laboratory; Ausubel, et al. (2011) Ed., *Current Protocols in Molecular Biology*, John Wiley & Sons, Inc., New York; Tijssen (1993) [Ed.] *Laboratory Techniques in Biochemistry and Molecular Biology: Hybridization With Nucleic Acid Probes, Part I, Theory and Nucleic Acid Preparation*, Elsevier, NY.

The invention provides for a primer pair for detecting the transgene/junction regions of event Pp009-401, event Pp009-415, or event Pp009-469. These primer pairs are used to produce an amplicons diagnostic for the events. In one aspect, any primer pair derived from SEQ ID NO: 7, SEQ ID NO: 8 and SEQ ID NO: 9 that, in a DNA amplification reaction produces an amplicon diagnostic for Kentucky bluegrass event Pp009-401, Pp009-415 and Pp009-469, respectively, is encompassed herein. In another aspect, any isolated DNA polynucleotide primer or primer pair comprising at least 11 (e.g., 12, 13, 14, 15, 16, 17, 18, 19, 20, 21, 22, 23, 24, 25, 26, 27, 28, or 29) contiguous nucleotides of SEQ ID NO: 7, SEQ ID NO: 8 and SEQ ID NO: 9, or its complement, useful in a DNA amplification method to produce an amplicon diagnostic for Kentucky bluegrass event Pp009-401, Pp009-415 and Pp009-469, respectively, is an aspect of the invention. In a particular aspect, Pp009-401, Pp009-415 and Pp009-469 event primer pairs that will produce a diagnostic amplicon for Kentucky bluegrass Pp009-401, Pp009-415 and Pp009-469, respectively, include, but are not limited to, a primer pair comprising Pp009-401 event primer 1 (SEQ ID NO: 1) and Pp009-401 event primer 2 (SEQ ID NO: 2); Pp009-415 event primer 1 (SEQ ID NO: 3) and Pp009-415 event primer 2 (SEQ ID NO: 4); and Pp009-469 event primer 1 (SEQ ID NO: 5) and Pp009-469 event primer 2 (SEQ ID NO: 6). In another aspect, amplicons diagnostic for Pp009-401, Pp009-415 and Pp009-469 comprise at least one junction sequence comprising SEQ ID NO: 7, SEQ ID NO: 8 and SEQ ID NO: 9, respectively.

The invention also provides for probes specific for the transgene/junction regions of event Pp009-401, event Pp009-415, or event Pp009-469. The probes are DNA molecules that hybridize specifically to a region within the 5' flanking region of the event and a region of the foreign/transgene DNA contiguous therewith. Exemplary probes include, but are not limited to DNA molecules comprising SEQ ID NO: 2 (event Pp009-401), SEQ ID NO: 4 (event Pp009-415), and SEQ ID NO: 6 (event Pp009-469). In another aspect, the probe comprises a sequence of between 50 bp and 500 bp, preferably of 100 to 350 bp which is at least 80%, 85%, 90%, 95%, 97%, 98%, 99%, or 100% identical to an event junction nucleotide sequence (e.g., nucleic acid molecule comprising SEQ ID NOs: 2, 4, 6, 7, 8, 9, or the complement thereof). In a particular embodiment, the probe comprises or specifically hybridizes to one or more of the nucleic acid molecules set forth in SEQ ID NOs: 2, 4, 6, 7, 8 or 9, complements thereof, or fragments thereof, under standard stringency conditions.

In another aspect, the probe comprises a sequence of between 50 bp and 500 bp, preferably of 100 to 350 bp which is at least 80%, 85%, 90%, 91% 92%, 93%, 94%, 95%, 96%, 97%, 98%, 99%, or 100% identical to the nucleotide sequence comprising SEQ ID NO: 10, SEQ ID NO: 11, SEQ ID NO: 12, SEQ ID NO: 13. In a particular embodiment, the probe comprises or specifically hybridizes to one or more of the nucleic acid molecules comprising SEQ ID NO: 10, SEQ ID NO: 11, SEQ ID NO: 12, SEQ ID NO: 13, complements thereof, or fragments thereof, under standard stringency conditions.

The present invention also encompasses variants of the nucleic acids described herein. The variant nucleic acids may encode amino acid substitutions that may be regarded as "conservative" where an amino acid is replaced with a different amino acid with broadly similar properties. Non-conservative substitutions are where amino acids are replaced with amino acids of a different type.

As is well known to those skilled in the art, altering the primary structure of a peptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptide's conformation. This substitution may be accomplished by changing the codon in the underlying nucleic acid.

Non-conservative substitutions are possible provided that these do not interrupt with the function of the encoded EPSPS enzyme or GA2OX protein. Broadly speaking, fewer non-conservative substitutions will be possible without altering the biological activity of the polypeptides.

Determination of the effect of any substitution (and, indeed, of any amino acid deletion or insertion) is wholly within the routine capabilities of the skilled person, who can readily determine whether a variant polypeptide retains the function of the encoded EPSPS enzyme or GA2OX protein. For example, when determining whether a variant of the polypeptide falls within the scope of the invention, the skilled person will determine whether the variant retains the activity of the encoded EPSPS enzyme or GA2OX protein activity at least 90%, 95%, 96%, 97%, 98%, 99% or 100% of the non-variant polypeptide. Activity may be measured by, for example, any standard measure such as the number of bases of a template sequence which can be replicated in a given time period.

Using the standard genetic code, further nucleic acids encoding the polypeptides may readily be conceived and manufactured by the skilled person. The nucleic acid may be DNA or RNA and, where it is a DNA molecule, it may for example comprise a cDNA or genomic DNA.

The invention encompasses variant nucleic acids encoding the polypeptide of the invention. The term "variant" in relation to a nucleic acid sequences means any substitution of, variation of, modification of, replacement of deletion of, or addition of one or more nucleic acid(s) from or to a polynucleotide sequence providing the resultant polypeptide sequence encoded by the polynucleotide exhibits at least the same properties as the polypeptide encoded by the basic sequence. The term therefore includes allelic variants and also includes a polynucleotide which substantially hybridizes to the polynucleotide sequence of the present invention. Such hybridization may occur at or between low and high stringency conditions. In general terms, low stringency conditions can be defined a hybridization in which the washing step takes place in a 0.330-0.825 M NaCl buffer solution at a temperature of about 40-48° C. below the calculated or actual melting temperature of the probe sequence (for example, about ambient laboratory temperature to about 55° C.), while high stringency conditions involve a wash in a 0.0165-0.0330 M NaCl buffer solution at a temperature of about 5-10° C. below the calculated or actual melting temperature of the probe (for example, about 65° C.). The buffer solution may, for example, be SSC buffer (0.15M NaCl and 0.015M tri-sodium citrate), with the low stringency wash taking place in 3×SSC buffer and the high stringency wash taking place in 0.1×SSC buffer. Steps involved in hybridization of nucleic acid sequences have been described for example in Sambrook, et al. (2001) (Eds.) *Molecular Cloning: A Laboratory Manual* [$3^{rd}$ Ed.] Cold Spring Harbor Laboratory, and by Hayrnes, et al. (1985) in *Nucleic Acid Hybridization, a Practical Approach* (IRL Press, DC).

Variant nucleic acids of the invention may be codon-optimized for expression in a particular host cell. Techniques for the manipulation of nucleic acids, such as, for example, for generating mutations in sequences, subcloning, labeling probes, sequencing, hybridization are well described in the scientific and patent literature. See, e.g., Sambrook, et al. (2001) (Eds.) *Molecular Cloning: A Laboratory Manual* ($3^{rd}$ Ed.) Cold Spring Harbor Laboratory; Ausubel, et al. (2011) Ed., *Current Protocols in Molecular Biology*, John Wiley & Sons, Inc., New York; Tijssen (1993) [Ed.] *Laboratory Techniques in Biochemistry and Molecular Biology: Hybridization With Nucleic Acid Probes, Part I, Theory and Nucleic Acid Preparation*, Elsevier, NY.

Sequence identity between nucleotide and amino acid sequences can be determined by comparing an alignment of the sequences. When an equivalent position in the compared sequences is occupied by the same amino acid or base, then the molecules are identical at that position. Scoring an alignment as a percentage of identity is a function of the number of identical amino acids or bases at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

In addition to the BLASTP computer program mentioned above, further suitable computer programs for carrying out sequence comparisons are widely available in the commercial and public sector. Examples include the MatGat program (Campanella, et al., 2003, BMC Bioinformatics 4: 29), the Gap program (Needleman & Wunsch, 1970, J. Mol. Biol. 48: 443-453) and the FASTA program (Altschul et al., 1990, J. Mol. Biol. 215: 403-410). MatGAT v2.03 is freely available and has also been submitted for public distribution to the Indiana University Biology Archive (IUBIO Archive). Gap and FASTA are available as part of the Accelrys GCG Package Version 11.1 (Accelrys, Cambridge, UK), formerly known as the GCG Wisconsin Package. The FASTA program can alternatively be accessed publicly from the European Bioinformatics Institute and the University of Virginia. FASTA may be used to search a sequence database with a given sequence or to compare two given sequences. Typically, default parameters set by the computer programs should be used when comparing sequences. The default parameters may change depending on the type and length of sequences being compared. A sequence comparison using the MatGAT program may use default parameters of Scoring Matrix=Blosum50, First Gap=16, Extending Gap=4 for DNA, and Scoring Matrix=Blosum50, First Gap=12, Extending Gap=2 for protein. A comparison using the FASTA program may use default parameters of Ktup=2, Scoring matrix=Blosum50, gap=−10 and ext=−2. Sequence identity can be determined using the MatGAT program v2.03 using default parameters as noted above.

Primers and probes based on the flanking genomic DNA and insert sequences disclosed herein can be used to confirm (and, if necessary, to correct) the disclosed DNA sequences by conventional methods, e.g., by re-cloning and sequencing such DNA molecules isolated from Kentucky bluegrass Pp009-401, Pp009-415, and Pp009-469, the seed of which is deposited with the ATCC having accession number PTA-120354, PTA-120353, and PTA-120355, respectively.

As used herein, “amplified DNA” or “amplicon” refers to the product of polynucleic acid amplification of a target polynucleic acid molecule that is part of a polynucleic acid template. For example, to determine whether a Kentucky bluegrass plant resulting from a sexual cross contains transgenic event genomic DNA from the Kentucky bluegrass event Pp009-401, Pp009-415 or Pp009-469, DNA extracted from a Kentucky bluegrass plant tissue sample may be subjected to polynucleic acid amplification method using a primer pair described herein (e.g., primer pair that includes a primer derived from flanking DNA in the genome of the Pp009-401, Pp009-415 or Pp009-469 plant adjacent to the insertion site of the inserted heterologous DNA (transgenic DNA), and a second primer derived from the inserted heterologous DNA to produce an amplicon diagnostic for the presence of the Pp009-401, Pp009-415 or Pp009-469 event DNA). The amplicon is of a length and has a polynucleotide sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs or more. In one aspect, the amplicon diagnostic for Pp009-401 is between 500-1000 base pairs (e.g., 720 base pairs). In another aspect, the amplicon diagnostic for Pp009-415 is between 500-1000 base pairs (e.g., 719 base pairs). In another aspect, the amplicon diagnostic for Pp009-469 is between 300-600 base pairs (e.g., 410 base pairs). The use of the term “amplicon” specifically excludes primer dimers that may be formed in the DNA thermal amplification reaction.

A member of a primer pair derived from the plant genomic sequence of Pp009-401, Pp009-415 and Pp009-469 may be located a distance from the inserted DNA molecule, this distance can range from one nucleotide base pair up to about twenty thousand nucleotide base pairs. Alternatively, a primer pair can be derived from flanking genomic sequence on both sides of the inserted heterologous DNA so as to produce an amplicon that includes the entire insert polynucleotide sequence (e.g., a primer pair that amplifies an inserted DNA molecule comprising the MluI expression cassette of pSCO761 DNA fragment that was transformed into Kentucky bluegrass, about 7,142 nucleotide base pairs, FIG. 2-4, for Pp009-401, Pp009-415 and Pp009-469, respectively).

Polynucleic acid amplification can be accomplished by any of the various polynucleic acid amplification methods known in the art, including the polymerase chain reaction (PCR) and are described, for example, in U.S. Pat. Nos. 4,683,195 and 4,683,202 and in PCR Protocols: A Guide to Methods and Applications, ed. Innis, et al. Academic Press, San Diego, 1990. PCR amplification methods have been developed to amplify up to 22 kb of genomic DNA and up to 42 kb of bacteriophage DNA (Cheng, et al. Proc. Natl. Acad. Sci. USA 91:5695-5699, 1994). These methods as well as other methods known in the art of DNA amplification may be used in the practice of the invention. Exemplary amplification conditions are illustrated in Table 1. It is understood that these conditions may be modified by those skilled in the art to produce an amplicon diagnostic for event Pp009-401, Pp009-415 or Pp009-469. Further, it is understood that these conditions may be modified by those skilled in the art to produce an amplicon diagnostic for the nucleic acid sequence of SEQ ID NO: 10, SEQ ID NO: 11, SEQ ID NO: 12, or SEQ ID NO: 13.

The sequence of the heterologous DNA insert or flanking genomic DNA from Kentucky bluegrass event Pp009-401, Pp009-415 and Pp009-469 can be verified by amplifying such DNA molecules from the event using primers derived from the sequences provided herein followed by standard DNA sequencing of the PCR amplicon or of the cloned DNA. DNA detection kits that are based on DNA amplification methods contain DNA primers that specifically amplify a diagnostic amplicon. The kit may provide an agarose gel based detection method or any number of methods of detecting the amplicon known in the art.

The amplicon produced by these methods may be detected by a plurality of techniques. For example, Genetic Bit Analysis (Nikiforov, et al. Nucleic Acid Res. 22:4167-4175, 1994) is a method where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled dideoxynucleotide triphosphate (ddNTPs) specific for the expected next base. Readout may be fluorescent or ELISA-based. A signal indicates presence of the insert/flanking sequence due to successful amplification, hybridization, and single base extension.

In pyrosequencing (Winge, Innov. Pharma. Tech. 00:18-24, 2000), an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. Deoxyribonucleotides (DNTPs) are added individually and the incorporation results in a light signal that is measured. A light signal indicates the presence of the transgene insert/flanking sequence due to successful amplification, hybridization, and single or multi-base extension.

Fluorescence Polarization (Chen, et al. Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

Taqman® (Applied Biosystems, Foster City, Calif.) is another method of detecting and quantifying the presence of a DNA sequence. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons (Tyagi, et al. Nature Biotech. 14:303-308, 1996) may also be used. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

In another embodiment, the invention provides for a marker nucleic acid molecule that comprises the nucleic acid sequence of SEQ ID NO: 1, 2, 3, 4, 5, 6, 7, 8, 9, 10, 11, 12, or 13 complements thereof, or fragments thereof. The marker nucleic acid molecule may share 80%, 85%, 90%, 91%, 92%, 93%, 94%, 95%, 97%, 98%, 99%, or 100% sequence identity with the nucleic acid sequence set forth in SEQ ID NO: 1-13, complements thereof, or fragments of either. The marker nucleic acid molecules may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al. eds., Wiley-Liss NY. The hybridization of the probe to the target DNA molecule can be detected by any number of methods known to those skilled in the art, including fluorescent tags, radioactive tags, antibody based tags, and chemiluminescent tags.

Kits

Kits comprising any of the products (e.g., nucleic acid molecules, primers, probes, markers) described herein are also provided. In one aspect, the kit comprises any primer pair derived from SEQ ID NO: 7, SEQ ID NO: 8 and SEQ ID NO: 9 that, in a DNA amplification reaction produces an amplicon diagnostic for Kentucky bluegrass event Pp009-401, Pp009-415 and Pp009-469, respectively. A kit may comprise any primer pair derived from the nucleotide sequence of SEQ ID NO: 10, SEQ ID NO: 11, SEQ ID NO: 12, or SEQ ID NO: 13. In another aspect, the kit comprises any primer pair derived from any of the genetic elements of pSCO761 diagnostic for Pp009-401, Pp009-415 or Pp009-469. In another aspect, the kit comprises any primer pair derived from SEQ ID NO: 10, SEQ ID NO: 11, SEQ ID NO: 12, or SEQ ID NO: 13. In another aspect, the kit comprises any isolated DNA polynucleotide primer or primer pair comprising at least 11 (e.g., 12, 13, 14, 15, 16, 17, 18, 19, 20, 21, 22, 23, 24, 25, 26, 27, 28, or 29) contiguous nucleotides of SEQ ID NO: 7, SEQ ID NO: 8 and SEQ ID NO: 9, or its complement, useful in a DNA amplification method to produce an amplicon diagnostic for Kentucky bluegrass event Pp009-401, Pp009-415 and Pp009-469, respectively. In a particular aspect, the kit comprises one or more of the following primer pairs: Pp009-401 event primer 1 (SEQ ID NO: 1) and Pp009-401 event primer 2 (SEQ ID NO: 2); Pp009-415 event primer 1 (SEQ ID NO: 3) and Pp009-415 event primer 2 (SEQ ID NO: 4); and Pp009-469 event primer 1 (SEQ ID NO: 5) and Pp009-469 event primer 2 (SEQ ID NO: 6).

In another aspect, the kit comprises a DNA specific for the transgene/junction regions of event Pp009-401, event Pp009-415, and/or event Pp009-469. In a particular aspect, the kit comprises a DNA molecule comprising SEQ ID NO: 2 (event Pp009-401), SEQ ID NO: 4 (event Pp009-415), SEQ ID NO: 6 (event Pp009-469), or combinations thereof. In another aspect, the kit comprises a DNA probe that specifically hybridizes to a nucleic acid molecule set forth in SEQ ID NOs: 7, 8, 9, 10, 11, 12, 13, complements thereof, fragments thereof, or combinations thereof, under standard stringency conditions.

Kits comprising any of the products (e.g., nucleic acid molecules, primers, probes, markers) described herein may include a solid support. The nucleic acid molecules, including but not limited to probes and primers, may be attached to a substrate. The nucleic acid molecules may be directly attached to the substrate or attached via a linker. The substrate includes but is not limited to smooth supports (e.g., metal, glass, plastic, silicon, and ceramic surfaces) as well as textured and porous materials. Substrate materials include, but are not limited to acrylics, carbon (e.g., graphite, carbon-fiber), cellulose (e.g., cellulose acetate), ceramics, controlled-pore glass, cross-linked polysaccharides (e.g., agarose or SEPHAROSE® (crosslinked, beaded-form of agarose), gels, glass (e.g., modified or functionalized glass), graphite, inorganic glasses, inorganic polymers, latex, mica, nanomaterials (e.g., highly oriented pyrolitic graphite (HOPG) nanosheets), nitrocellulose, NYLON® (aliphatic polyamides), optical fiber bundles, organic polymers, paper, plastics, polacryloylmorpholide, poly(4-methylbutene), poly(ethylene terephthalate), poly(vinyl butyrate), polybutylene, polydimethylsiloxane (PDMS), polyethylene, polyformaldehyde, polymethacrylate, polypropylene, polysaccharides, polystyrene, polyurethanes, polyvinylidene difluoride (PVDF), quartz, rayon, resins, rubbers, semiconductor material, silica, silicon (e.g., surface-oxidized silicon), sulfide, and TEFLON® (Polytetrafluoroethylene (PTFE)).

Substrates need not be flat and can include any type of shape including spherical shapes (e.g., beads) or cylindrical shapes (e.g., fibers). The nucleic acid molecules, including but not limited to probes and primers, may be attached to any portion of the solid support (e.g., may be attached to an interior portion of a porous solid support material).

Substrates may be patterned, where a pattern (e.g., stripes, swirls, lines, triangles, rectangles, circles, arcs, checks, plaids, diagonals, arrows, squares, or cross-hatches) is etched, printed, embedded, or layered onto a substrate. For example, the probes and primers described herein may be arranged in an array on a solid support (e.g., attached to the support in a pattern). The substrate can be substantially flat or planar. Alternatively, the surface can be rounded or contoured. Exemplary contours that can be included on a surface are wells, depressions, pillars, ridges, and channels.

The nucleic acid molecules, including but not limited to probes and primers, may be attached to a substrate through a stable chemical or physical interaction. The attachment may be through a covalent bond. However, attachments need not be covalent or permanent. For example, the materials may be attached to a substrate through a "spacer molecule" or "linker group." Such spacer molecules are molecules that have a first portion that attaches to the nucleic acid molecule and a second portion that attaches to the substrate. Thus, when attached to the substrate, the spacer molecule separates the substrate and the nucleic acid, but is attached to both. Methods of attaching nucleic acids to a substrate are well known in the art, and include but are not limited to chemical coupling.

Kits comprising any of the products (e.g., nucleic acid molecules, primers, probes, markers) described herein may be in a buffer or solution. For example, the probes and primers may be provided suspended in a buffer. The probes and primers described herein may be lyophilized.

The sequences discloses herein, probes and primers, may be labeled. The label may be a chemiluminescent label, paramagnetic label, an MRI contrast agent, fluorescent label, bioluminescent label, or radioactive label.

Areas Comprising the Events

Kentucky bluegrass events Pp009-401, Pp009-415 and Pp009-469 are tolerant to glyphosate herbicide and possess enhanced turfgrass quality. Grasses comprising these events are useful in a turfgrass stand. As such, the invention provides for turfgrass stands comprising Kentucky bluegrass event Pp009-401, Pp009-415 and/or Pp009-469. The turfgrass stand may be cultivated in private and public areas. In a particular aspect, the turfgrass stand comprising Pp009-401, Pp009-415 and/or Pp009-469 is grown or located on a sports field (e.g., golf course), home lawn or public ground. In another aspect, the invention provides for a turfgrass stand wherein at least 50%, 75%, 90%, or more of the turfgrass stand comprises Kentucky bluegrass event Pp009-401, Pp009-415 and/or Pp009-469.

Turfgrass stands comprising events Pp009-401, Pp009-415 and/or Pp009-469 can be effectively managed for weed control by the application of a glyphosate containing herbicide. As such, the invention provides for methods of controlling weeds in a turfgrass stand comprising applying an effective amount of glyphosate to a turfgrass stand comprising events Pp009-401, Pp009-415 and/or Pp009-469.

Variant EPSPS DNA Molecules, Vectors, and Host Cells

Another aspect of the invention pertains to nucleic acid molecules that encode the variant EPSPS. The nucleic acids may be present in whole cells, in a cell lysate, or in a partially purified or substantially pure form. A nucleic acid may be isolated by purification away from other cellular components or other contaminants (e.g., other cellular nucleic acids or proteins) by standard techniques, including alkaline/SDS treatment, CsCl banding, column chromatography, agarose gel electrophoresis and others well known in the art. A nucleic acid of the invention may be, for example, DNA or RNA and may or may not contain intronic sequences. The nucleic acid may be a cDNA molecule. Exemplary nucleic acids may be a DNA molecule with at least about 80%, 81%, 82%, 83%, 84%, 85%, 86%, 87%, 88%, 89%, 90%, 91%, 92%, 93%, 94%, 95%, 96%, 97%, 98%, or 99% identity to the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13. Nucleic acids of the invention may be obtained using standard molecular biology techniques. See Ausubel, et al. (2011) *Current Protocols in Molecular Biology*, John Wiley & Sons, Inc.

Expression vectors, either as individual expression vectors or as libraries of expression vectors, comprising the ligand-binding region encoding sequences may be introduced into a genome or into the cytoplasm or a nucleus of a cell and expressed by a variety of conventional techniques, well described in the scientific and patent literature. See, e.g., Sambrook, et al. (2001) [Eds.] *Molecular Cloning: A Laboratory Manual* (3rd Ed.) Cold Spring Harbor Laboratory; Ausubel, et al. (2011) [Ed.] *Current Protocols in Molecular Biology*, John Wiley & Sons, Inc.; Knäblein (2006) "Plant-based Expression of Biopharmaceuticals." *Encylopedia of Molecular Cell Biology and Molecular Medicine*; and Lindbo *BMC Biotechnology* 2007, 7:52.

The nucleic acids can be expressed in expression cassettes, vectors or viruses which are stably or transiently expressed in cells (e.g., episomal expression systems). Selection markers can be incorporated into expression cassettes and vectors to confer a selectable phenotype on transformed cells and sequences. For example, selection markers can code for episomal maintenance and replication such that integration into the host genome is not required. For example, the marker may encode antibiotic resistance (e.g., chloramphenicol, kanamycin, G418, bleomycin, hygromycin) or herbicide resistance (e.g., chlorosulfurone or Basta) to permit selection of those cells transformed with the desired DNA sequences. See, e.g., Ausubel, et al. (2011) [Ed.] *Current Protocols in Molecular Biology* John Wiley & Sons, Inc.; Walker & Papley (2009) *Molecular Biology and Biotechnology* [5th Ed.] Royal Society of Chemistry; and Twyman, et al. (2003) "Molecular farming in plants: host systems and expression technology." *TRENDS in Biotechology* 21(12): 570-578. Because selectable marker genes conferring resistance to substrates like neomycin or hygromycin can only be utilized in tissue culture, chemoresistance genes are also used as selectable markers in vitro and in vivo.

To enable cellular expression of the polynucleotides of the present invention, a nucleic acid construct according to the present invention may be used, which includes at least a coding region of one of the above nucleic acid sequences, and further includes at least one cis acting regulatory element. Preferably, the promoter utilized by the nucleic acid construct of the present invention is active in the specific cell population transformed. Examples of cell type-specific and/or tissue-specific promoters are well-known in the art. See Kole, et al. (2012) [Ed.] *Handbook of Bioenergy Crop Plants* CRC Press; Fernandez & Hoeffler (1999) *Gene Expression Systems: Using Nature for the Art of Expression* Academic Press. The nucleic acid construct of the present invention can further include an enhancer, which can be adjacent or distant to the promoter sequence and can function in up regulating the transcription therefrom.

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible for propagation in cells, or integration in a gene and a tissue of choice. The construct according to the present invention can be, for example, a plasmid, a bacmid, a phagemid, a cosmid, a phage, a virus, for example tobacco mosaic virus (TMV), potato virus X, or cowpea mosaic virus, or an artificial chromosome.

Examples of suitable constructs include, but are not limited to, pcDNA3, pcDNA3.1 (+/−), pGL3, PzeoSV2 (+/−), pDisplay, pEF/myc/cyto, pCMV/myc/cyto each of which is commercially available from Life Technologies (Carlsbad, Calif.) Examples of retroviral vector and packaging systems are those sold by Clontech (San Diego, Calif.), including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5' LTR promoter. Many plant expression vectors are based on Ti plasmid of *Agrobacterium tumefaciens*.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

A host cell can be any prokaryotic or eukaryotic cell. For example, protein of the invention can be produced in bacterial cells such as *E. coli*, insect cells, yeast, plant or mammalian cells (e.g., Chinese hamster ovary cells (CHO), COS, HEK293 cells). Other suitable host cells are known to those skilled in the art. Alternatively, polypeptides of the present invention can be produced in insect cells using baculovirus expression vectors. Baculovirus vectors available for expression of proteins in cultured insect cells (e.g., SF9 cells) include the pAc series (Smith, et al. (1983) *Mol. Cell. Biol.* 3: 2156-2165) and the pVL series (Lucklow and Summers (1989) *Virology* 170: 31-39).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (2001) [Eds.] *Molecular Cloning: A Laboratory Manual* (3rd Ed.) Cold Spring Harbor Laboratory.

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell. See, e.g., Sambrook, et al. (2001) (Eds.) *Molecular Cloning: A Laboratory Manual* (3rd Ed.) Cold Spring Harbor Laboratory and Walker & Papley (2009) *Molecular Biology and Biotechnology* [5th Ed.] Royal Society of Chemistry.

A host cell of the invention, such as a prokaryotic or eukaryotic host cell in culture, can be used to produce (i.e., express) protein of the invention. Accordingly, the invention further provides methods for producing proteins of the invention using the host cells of the invention. In one embodiment, the method comprises culturing the host cell of the present invention (into which a recombinant expression vector encoding protein of the invention has been introduced) in a suitable medium such that the protein of the invention is produced. In another embodiment, the method further comprises isolating protein of the invention from the medium or the host cell.

After the expression vector is introduced into the cells, the transfected cells are cultured under conditions favoring expression of the receptor, fragment, or variant of interest, which is then recovered from the culture using standard techniques. Examples of such techniques are well known in the art. See, e.g., WO 00/06593.

Seed Deposit Information

Reference seed comprising events Pp009-401, Pp009-415, and Pp009-469 were deposited at the ATCC (ATCC Patent Depository, 10801 University Blvd., Manassas, Va. 20110) on May 17, 2013, under the Budapest Treaty, as ATCC accession numbers PTA-120354, PTA-120353, and PTA-120355, respectively, and the viability thereof was confirmed on Jun. 5, 2013. All restrictions on the availability to the public of the deposited material will be irrevocably removed upon the granting of a patent on the present application.

Expression of Transgenes in Plants

The invention also provides for methods of producing plants comprising a nucleic acid molecule of the nucleotide sequence of SEQ ID NOs: 1-13 by plant transgenesis, a first stage comprising the integration, into plant cells of a nucleic acid molecule of the nucleotide sequence of SEQ ID NOs: 1-13, the second stage comprising the regeneration of the plant from the transformed cells according to the invention. The transformation may be obtained by any appropriate means known in the art. By using nucleic acid molecules encoding EPSPS it is possible to produce plants by means of recombinant DNA techniques (for example by an antisense, a ribozyme or a cosuppression approach) exhibiting glyphosate resistance. Therefore in another embodiment of the invention the plant cells of the invention are further characterized by glyphosate resistance as compared to corresponding cells from wild-type plants.

A plurality of techniques is available by which DNA can be inserted into a plant host cell. These techniques include the transformation of plant cells by T-DNA using *Agrobacterium tumefaciens* or *Agrobacterium rhizogenes* as a transforming agent, the fusion of protoplasts, injection, electroporation of DNA, insertion of DNA by the biolistic approach and other possibilities.

The use of the Agrobacteria-mediated transformation of plant cells has been extensively investigated and sufficiently described in EP 120 516; Hoekema, In: The Binary Plant Vector System, Offsetdrukkerij Kanters B. V., Alblasserdam (1985), Chapter V; Fraley et al, Crit. Rev. Plant Sci. 4 (1993), 1-46 and An, et al. EMBO J. 4 (1985), 277-287. Regarding the transformation of potatoes see for instance Rocha-Sosa et al. (EMBO J. 8 (1989), 29-33).

The transformation of monocotyledonous plants by means of *Agrobacterium*-based vectors has also been described (Chan, et al. Plant Mol. Biol. 22 (1993), 491-506; Hiei, et al. Plant J. 6 (1994) 271-282; Deng et al, Science in China 33 (1990), 28-34; Wilmink et al, Plant Cell Reports 11 (1992), 76-80; May, et al. Bio/Technology 13 (1995), 486-492; Conner and Dormisse, Int. J. Plant Sci. 153 (1992), 550-555; Ritchie et al. Transgenic Res. 2 (1993), 252-265). An alternative system for transforming monocotyledonous plants is the transformation by the biolistic approach (Wan and Lemaux, Plant Physiol. 104 (1994), 37-48; Vasil, et al. Bio/Technology 11 (1993), 1553-1558; Ritala, et al. Plant Mol. Biol. 24 (1994) 317-325; Spencer, et al. Theor. Appl. Genet. 79 (1990), 625-631), protoplast transformation, electroporation of partially permeabilized cells, insertion of DNA via glass fibers. The transformation of maize in particular has been repeatedly described in the literature (see for instance WO 95/06128, EP 0 513 849, EP 0 465 875, EP 29 24 35; Fromm et al, Biotechnology 8, (1990), 833-844; Gordon-Kamm, et al. Plant Cell 2, (1990), 603-618; Koziel, et al. Biotechnology 11 (1993), 194-200; Moroc, et al. Theor. Appl. Genet. 80, (1990), 721-726).

The successful transformation of other types of cereals has also been described for instance of barley (Wan and Lemaux, supra; Ritala, et al. supra, Krens, et al. Nature 296 (1982), 72-74) and wheat (Nehra, et al. Plant J. 5 (1994), 285-297).

One series of methods consists in bombarding cells or protoplasts with particles to which DNA sequences are attached. Nucleic acids comprising the sequence of SEQ ID NOs: 1, 2, 3, 4, 5, 6, 7, 8, 9, 10, 11, 12, or 13 may be carried by the same particles or by different bombardments. Another method utilizes a chimeric gene inserted into an *Agrobacterium rhizogenes* Ri or *Agrobacterium tumefaciens* Ti plasmid. Other methods may be used, such as microinjection or electroporation. Persons skilled in the art will choose the appropriate method according to the nature of the plant, in particular its monocotyledonous or dicotyledonous character.

The nucleic acid molecule of the nucleotide sequence of SEQ ID NO: 1-13 may be expressed in a host cell. The host cells may be cells of microorganisms, including but not limited to bacterial cells (e.g., *E. coli*) and yeast cells. The preparation of such host cells for the production of recombinant EPSPS can be carried out by methods known to those skilled in the art.

An overview of different expression systems is for instance contained in Methods in Enzymology 153 (1987), 385-516, in Bitter et al. (Methods in Enzymology 153 (1987), 516-544) and in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al, Methods in Molecular Biology 75 (1997), 427-440). An overview of yeast expression systems is for instance given by Hensing et al. (Antonie van Leuwenhoek 67 (1995), 261-279), Bussineau et al. (Developments in Biological Standardization 83 (1994), 13-19), Gellissen et al. (Antonie van Leuwenhoek 62 (1992), 79-93, Fleer (Current Opinion in Biotechnology 3 (1992), 486-496), Vedvick (Current Opinion in Biotechnology 2 (1991), 742-745) and Buckholz (Bio/Technology 9 (1991), 1067-1072).

The transformation of the host cell with DNA encoding an EPSPS can be carried out by standard methods, as for instance described in Sambrook, et al. (2001) *Molec. Cloning: Lab. Manual* [3rd Ed] Cold Spring Harbor Laboratory Press. See, also, Burke, et al. (2000) *Methods in Yeast Genetics* Cold Spring Harbor Laboratory Press. The host cell is cultured in nutrient media meeting the requirements of the particular host cell used, in particular in respect of the pH value, temperature, salt concentration, aeration, antibiotics, vitamins, or trace elements.

The invention also provides to transgenic plant cells transformed by a nucleic acid molecule of the nucleotide sequence of SEQ ID NO: 1-13 or a vector of the invention or descended from such cells, the nucleic acid molecule which encodes the protein that has the biological activity of an EPSPS being under the control of regulatory elements permitting the transcription of a translatable mRNA in plant cells.

Generally, any promoter active in plant cells is suitable to express the nucleic acid molecules in plant cells. The promoter can be so chosen that the expression in the plants of the invention occurs constitutively or only in a particular tissue, at a particular time of plant development or at a time determined by external influences. The promoter may be homologous or heterologous to the plant.

Suitable promoters are for instance the promoter of 35S RNA of the Cauliflower Mosaic Virus (See, e.g., U.S. Pat. No. 5,352,605) and the ubiquitin-promoter (See, e.g., U.S. Pat. No. 5,614,399) which lend themselves to constitutive expression, the patatin gene promoter B33 (Rocha-Sosa, et al. EMBO J. 8 (1989), 23-29) which lends itself to a tuber-specific expression in potatoes or a promoter ensuring expression in photosynthetically active tissues only, for instance the ST-LS1 promoter (Stockhaus, et al. Proc. Natl. Acad. Sci. USA 84 (1987), 7943-7947; Stockhaus, et al. EMBO, J. 8 (1989) 2445-2451), the Ca/b-promoter (see for instance U.S. Pat. Nos. 5,656,496, 5,639,952, Bansal, et al. Proc. Natl. Acad. Sci. USA 89 (1992), 3654-3658) and the Rubisco SSU promoter (see for instance U.S. Pat. Nos. 5,034,322; 4,962,028) or the glutelin promoter from wheat which lends itself to endosperm-specific expression (HMW promoter) (Anderson, Theoretical and Applied Genetics 96, (1998), 568-576, Thomas, Plant Cell 2 (12), (1990), 1171-1180), the glutelin promoter from rice (Takaiwa, Plant Mol. Biol. 30(6) (1996), 1207-1221, Yoshihara, FEBS Lett. 383 (1996), 213-218, Yoshihara, Plant and Cell Physiology 37 (1996), 107-111), the shrunken promoter from maize (Maas, EMBO J. 8 (11) (1990), 3447-3452, Werr, Mol. Gen. Genet. 202(3) (1986), 471-475, Werr, Mol. Gen. Genet. 212(2), (1988), 342-350), the USP promoter, the phaseolin promoter (Sengupta-Gopalan, Proc. Natl. Acad. Sci. USA 82 (1985), 3320-3324, Bustos, Plant Cell 1 (9) (1989), 839-853) or promoters of zein genes from maize (Pedersen, et al. Cell 29 (1982), 1015-1026; Quatroccio, et al. Plant Mol. Biol. 15 (1990), 81-93). However, promoters which are only activated at a point in time determined by external influences can also be used (see for instance WO 93/07279). In this connection, promoters of heat shock proteins which permit simple induction may be of particular interest. Moreover, seed-specific promoters such as the USP promoter from *Vicia faba* which ensures a seed-specific expression in *Vicia faba* and other plants may be used (Fiedler, et al. Plant Mol. Biol. 22 (1993), 669-679; Baumlein, et al. Mol. Gen. Genet. 225 (1991), 459-467). Moreover, fruit-specific promoters, such as described in WO 91/01373 may be used. Shoot-preferred promoters may be used.

Moreover, a termination sequence may be present, which serves to terminate transcription correctly and to add a poly-A-tail to the transcript, which is believed to have a function in the stabilization of the transcripts. Such elements are described in the literature (see for instance Gielen, et al. EMBO J. 8 (1989), 23-29) and can be replaced at will.

Such cells can be distinguished from naturally occurring plant cells inter alia by the fact that they contain a nucleic acid molecule of the invention which does not naturally occur in these cells. For example, a person skill in the art can screen for transformants by treating the plants with an herbicide comprising glyphosate. Moreover, such transgenic plant cells of the invention can be distinguished from naturally occurring plant cells in that they contain at least one copy of the nucleic acid molecule of the invention stably integrated in their genome (e.g., the plants are tolerant to glyphosate).

Moreover, the plant cells of the invention can preferably be distinguished from naturally occurring plant cells by at least one of the following features: If the inserted nucleic acid molecule of the invention is heterologous to the plant cell, then the transgenic plant cells are found to have transcripts of the inserted nucleic acid molecules of the invention. The latter can be detected for instance by Northern blot analysis. The plants cells of the invention preferably contain a protein encoded by an inserted nucleic acid molecule of the invention. This can be shown for instance by immunological methods, in particular by Western blot analysis.

The present invention also provides the plants obtainable by regeneration of the transgenic plant cells of the invention. Furthermore, also plants containing the above-described transformed plant cells are described herein. Transgenic plant cells can be regenerated to whole plants according to methods known to a person skilled in the art.

TABLE 1

| Sequences | | |
|---|---|---|
| Sequence Identifier | Nucleic Acid | Type |
| 1 | 401 UBB1 Dil 3-1 | primer for transgene/genomic junction |
| 2 | 401 UBB1 Dil 5-2 | primer for genomic DNA sequence flanking the 5' end |
| 3 | 415 GOB 1 Dil 3-1 | primer for transgene/genomic junction |
| 4 | 415 GOB 1 Dil 5-2 | primer for genomic DNA sequence flanking the 5' end |
| 5 | 469 GOB 1 Dil 3-1 | primer for transgene/genomic junction |
| 6 | 469 GOB 1 Dil 5-5 | primer for genomic DNA sequence flanking the 5' end |
| 7 | Pp009-401 transgene/genomic/chromosomal flanking DNA sequence | Event |
| 8 | Pp009-415 transgene/genomic/chromosomal flanking DNA sequence | Event |
| 9 | Pp009-469 transgene/genomic/chromosomal flanking DNA sequence | Event |

TABLE 1-continued

| Sequences | | |
|---|---|---|
| Sequence Identifier | Nucleic Acid | Type |
| 10 | EPSPS cassette | transgene cassette |
| 11 | GAO2X cassette | transgene cassette |
| 12 | variant EPSPS transgene | transgene (cDNA) |
| 13 | GAO2X transgene | transgene (cDNA) |

All publications (e.g., Non-Patent Literature), patents, patent application publications, and patent applications mentioned in this specification are indicative of the level of skill of those skilled in the art to which this invention pertains. All such publications (e.g., Non-Patent Literature), patents, patent application publications, and patent applications are herein incorporated by reference to the same extent as if each individual publication, patent, patent application publication, or patent application was specifically and individually indicated to be incorporated by reference.

The following examples show various embodiments of the invention. It should be appreciated by those of skill in the art that modifications can be made without departing from the spirit and scope of the invention.

EXAMPLES

Example 1

Events Pp009-401, Pp009-415, and Pp009-469

The transgenic Kentucky bluegrass events Pp009-401, Pp009-415, and Pp009-469 were generated by microprojectile bombardment of Kentucky bluegrass callus material using a linear DNA fragment derived from pSCO761 (FIG. 1), the transgene insert of the invention. This DNA fragment contains two transgene expression cassettes that confer glyphosate and enhanced turfgrass characteristics. The first cassette includes the rice ubiquitin promoter (P-Os.UBQ, also referred to as P-rUBQ) and rice actin 1 intron (I-Os-.Act1, also referred to as ract intron) (see U.S. Pat. No. 5,641,876, incorporated by reference herein), operably connected to a glyphosate tolerant 5-enol-pyruvylshikimate-3-phosphate synthase (EPSPS) from *Arabidopsis* and operably connected to a *Zea mays* alcohol dehydrogenase transcriptional terminator. The second transgene expression cassette includes the Os.GOS2 promoter, operably connected to gibberellic acid 2-oxidase from spinach (Lee, et al. Plant Physiology, May 2005, Vol. 138, pp. 243-254, incorporated by reference herein in its entirety) and operably connected to a *Solanum pennellii* histone H1 gene transcriptional terminator.

Post-bombardment, glyphosate-tolerant transgenic calli were selected on media containing 0.5 mM glyphosate and plants were subsequently regenerated on media containing 0.1 mM glyphosate. Transgenic events were produced and events Pp009-401, Pp009-415 and Pp009-469 were selected from this population based on a superior combination of characteristics, including glyphosate tolerance and enhanced turfgrass quality.

Example 2

Tolerance to Glyphosate Vegetative Injury

Kentucky bluegrass events Pp009-401, Pp009-415, and Pp009-469 were tested for tolerance to glyphosate vegetative injury. Kentucky bluegrass plants comprising events Pp009-401, Pp009-415, and Pp009-469 showed no damage to Roundup® Pro (glyphosate containing herbicide formulation) sprayed in a booth at 3.0 lbs acid equivalence or an amount equivalent to 128 ounces Roundup® Pro per acre. The standard recommended rate is 1.25 to 2.5% Roundup® Pro or amount equivalent to 32 to 64 ounces Roundup® Pro per acre. Therefore, treating a turfgrass stand comprising Kentucky bluegrass Pp009-401, Pp009-415, and/or Pp009-469, with a glyphosate containing herbicide, is useful for controlling weeds and other unwanted plants in the turfgrass stand.

Example 3

DNA Sequences of the Genomic Regions Adjacent to the Transgene

The DNA sequences of the genomic regions adjacent to the transgene insert were determined by isolation of the DNA molecules using Clontech's Universal Genome Walker™ Kit (Clontech Laboratories Inc, Mountain View, Calif.) (part no 638904) to clone plant genomic sequences that flank a bombardment-mediated inserted copy of pSCO761. Genomic DNA (3 μg) of Kentucky bluegrass Pp009-401, Pp009-415, and Pp009-469 were digested completely with blunt-cutter enzyme BsaBI, selected for the apparent lack of internal sites within the pSCO761 cassette. After verifying an effective digestion, DNA was then purified using the Promega Wizard® SV gel/PCR cleanup kit (Promega Corporation, Cat no A9281), which collects DNA on a binding membrane on a spin column. DNA was then eluted with nuclease-free water (20 μL). A 4-μL sample of purified DNA digest was then ligated overnight at 16° C. to a short (50 bases long) double-stranded, blunt-ended adaptor, which contains sequence for binding two nested oligomers (AP1 and AP2) included in the Geomewalker™ kit. To each 8-μL ligation reaction 65 μL water and 7.2 μL 10×TE was added. This finished "Genomewalker library" was used as a template for two successive PCR reactions, the first using the outermost linker primer (AP1), and the outermost "flanking" primers designed from pSCO761.

Two sets of nested oligonucleotides had been designed that primed in reverse at a location within 100 bp of either end of the pSCO761 cassette, allowing PCR amplification of a flanking sequence adjacent to either the GOS2 promoter at one end, or the RUBQ promoter at the other end. They have been designated PRU761 fl-1 PRU761 fl-2, PG0761 fl-1, and PGO761 fl-2. This first PCR reaction (PCR1) is done as a set of two per transgenic line, using each of the transgene-specific primers (PRU761 fl-1 and PGO761 fl-1) in combination with Genomewalker™ primer AP1. Since the nearest genomic BsaBI site to insertion sites of pSCO761 are unknown, PCR conditions are designed to amplify long sequences, up to 6 kb. A kit containing a Taq polymerase optimized for long-distance PCR (Advantage 2 PCR kit) (Clontech Laboratories Inc, Mountain View, Calif.) (part no 639206) was used.

Two PCR programs were designed, based on recommendations by the kit. The first PCR reaction used a program named FLANK1: 95° C.-2', (94° C.-25", 64° C.-6')×7, (94° C.-25", 60° C.-6')×30, 72° C.-10'. After the PCR1 run was complete, an aliquot of the reaction was diluted 1/50 in sterile water for use as a template for PCR2. This next PCR reaction enriches for sequence flanking the transgene, by priming the products of PCR 1 with nested primers specific to either the Genomewalker™ linker (AP2) or the transgene (PGO761 fl-2 or PRU761 fl-2). To each reaction 1 μL diluted PCR1 template and 1 μL 10 mM transgene-specific nested primer 2 was added; the diluted PCR1 reaction using PG0761 fl-1/AP1 was the template for PG0761 fl-2/AP2, and the diluted PCR1 reaction using PRU761 fl-1/AP1 was the template for PRU761 fl-2/AP2. The $2^{nd}$ PCR reaction used a program named FLANK2: 95° C.-2', (94° C.-25", 64° C.-25", 68° C.-6')x5, (94° C.-25", 60° C.-25", 68° C.-6')x21, 72° C.-10'.

The completed PCR2 reactions are resolved by electrophoresis on a preparative agarose gel. Intensely-staining bands were each excised separately using a clean scalpel blade, for cloning/sequencing. Each band was given a designation based on the transgenic line, the primer sets used, the restriction endonuclease that generated the library, and finally the order of band recovery, if multiple bands were produced. A 0.80-kb fragment generated from the Pp009-401 BsaBI library using the PRU761 primer set (priming P-RUBQ in reverse) was named 401-UB-B-1. Likewise, a 0.80-kb fragment generated from Pp009-415 BsaBI library using the PG0761 primer set (priming P-GOS2 in reverse) was named 415-GO-B-1. A 1.0-kb fragment generated from the Pp009-469 BsaBI library using the PG0761 primer set was named 469-GO-B-1. Fragments in excised gel slices were extracted using the Wizard®SV—gel/PCR cleanup kit (Promega Corp, Madison Wis.) (Part no A9281), according to the instructions by the manufacturer. The gel slice is dissolved in a special binding buffer included with the kit, and collecting the DNA by passage through a spin column with a binding membrane. DNA was eluted from the membrane with 24 μL sterile water, and cloned into a vector designed for cloning and sequencing PCR fragments (TOPO®TA Cloning kit, Invitrogen, by Life Technologies™) (Part no K4575-01). Each cloning reaction used 4 μL extracted fragment in a 6-μL reaction volume with 1 μL each TOPO vector (pCR™4-TOPO®), and salt solution provided in the kit. Reactions were incubated for at least 5' at room temperature, and 1 L each was then used to transform aliquots of *E. coli* (One Shot® TOP10) competent cells provided with the kit. Cells were incubated on ice for 30', then heat shocked at 43° C. for 30", then incubated for 1 H with shaking at 37° C. before plating on LB agar medium containing 50 mg/L carbenicillin, and culturing overnight at 37° C. Viable colonies were then screened for the presence of expected-sized insert by colony PCR amplification using primers (T3 TOPO long and T7 TOPO long) designed to the T3 and T7 sequences of the TOPO vector cloning site. Clones showing inserts of expected size were sent to Cornell University's Biotechnology Resource Center for bidirectional sequencing from the T3 and T7 sites, using T3 TOPO long and T7 TOPO long to prime the sequencing reactions.

Sequence data generated from these fragments was analyzed, and mapped for the BsaBI cloning site to the Genomewalker linker at one end, and for pSCO761 sequence (either P-RUBQ or P-GOS2) junction at the other. DNA sequence between the junction and the BsaBI cloning site was then verified to be unlike pSCO761 by comparing against the complete sequence of the MluI cassette of pSCO761 using L-ALIGN software (Sequence identity to pSCO761 would indicate a tandem repeat). If the sequence was dissimilar to pSCO761, it was postulated to be host plant genomic sequence flanking a pSCO761 insertion site, and was subjected to BLAST searches using NCBI and TIGR monocot transcript databases. Any strong "hits" to either a cloned cDNA or a non-coding sequence from a genomic library was also noted as part of the record for that fragment. The DNA sequence of the genomic/transgene region DNA molecule is illustrated in FIGS. 2, 3 and 4 for Pp009-401, Pp009-415, and Pp009-469, respectively.

Example 4

Presence of the Transgene/Genomic DNA in a Kentucky Bluegrass

The presence of the transgene/genomic DNA in a Kentucky bluegrass sample was verified by using PCR to generate a transgene/genomic junction region amplicon using alternate primers to those originally used to clone the Genomewalker library fragment. For Pp009-401, the transgene/genomic junction region amplicon is produced using one primer (SEQ ID NO: 1), designed to an area within the genomic DNA sequence flanking the 5' end of the insert paired with a second primer (SEQ ID NO: 2) associated within the rice ubiquitin promoter of the inserted transgene DNA. For Pp009-415, the transgene/genomic junction region amplicon is produced using one primer (SEQ ID NO: 3), designed to an area within the genomic DNA sequence flanking the 5' end of the insert paired with a second primer (SEQ ID NO: 4) associated within the GOS2 promoter of the inserted transgene DNA. For Pp009-469, the transgene/genomic junction region amplicon is produced using one primer (SEQ ID NO: 5), designed to an area within the genomic DNA sequence flanking the 5' end of the insert paired with a second primer (SEQ ID NO: 6) associated within the RUBQ promoter of the inserted transgene DNA. The junction amplicons were produced from about 10 ng of leaf genomic DNA as a template, 10 pmol of each primer, and the GoTaq®Flexi DNA Polymerase system (Promega Corp, Madison Wis.) (Part no M8295) in a 50 μl reaction volume. The amplification of the reactions was performed under the following cycling conditions: 95° C.-2', (94° C.-45", 65° C.-45", 72° C.-1')x40, 72° C.-10'.

Kentucky bluegrass genomic DNA flanking sequence of the transgenic insertion was determined for event Pp009-401, Pp009-415 and Pp009-469 by sequencing the Genome Walker™-derived amplification products and alignment to known transgene sequence. A 5' region of the transgene insertion site was sequenced, this region comprises a transgene/genomic DNA sequence of 770 nucleotide base pairs (bps) (SEQ ID NO: 7) for Pp009-401, 832 nucleotide base pairs (bps) (SEQ ID NO: 8) for Pp009-415, 516 nucleotide base pairs (bps) (SEQ ID NO: 9) for Pp009-469.

The junction sequences, SEQ ID NO: 1 and SEQ ID NO: 2 (FIG. 5), SEQ ID NO: 3 and SEQ ID NO: 4 (FIG. 6), SEQ ID NO: 5 and SEQ ID NO: 6 (FIG. 7) are novel DNA sequences from event Pp009-401, Pp009-415 and Pp009-469, respectively, and are diagnostic for Kentucky bluegrass plant event Pp009-401, Pp009-415, and Pp009-469, respectively, and its progeny. The junction sequences in SEQ ID NO: 1 and SEQ ID NO: 2 comprise polynucleotides on each side of an insertion site of a transgene sequence fragment and Kentucky bluegrass genomic DNA. The sequence SEQ ID NO: 1 is found at nucleotide position 15-43 of SEQ ID NO: 7, the 5' region of the transgene insertion site for PP009-401. The sequence SEQ ID NO: 3 is found at nucleotide position 32-56 of SEQ ID NO: 8, the 5' region of the transgene insertion site for PP009-415. The sequence SEQ ID NO: 5 is found at nucleotide position 76-106 of SEQ ID NO: 9, the 5' region of the transgene insertion site for Pp009-469.

Example 5

Specificity of the Cloned Transgene/Genomic Flanking Sequences

The specificity of the cloned transgene/genomic flanking sequences SEQ ID Nos. 7, 8, and 9 to transgenic lines Pp009-401, Pp0090-415 and Pp009-469 respectively, was tested by a series of PCR reactions using primer pairs Seq ID NO: 1 and 2 (designed to Pp009-401 cloned fragment Seq ID NO: 7), Seq ID NO: 3 and 4 (designed to Pp009-415 cloned fragment Seq ID NO:8), and Seq ID NO: 5 and 6 (designed to Pp009-469 cloned fragment Seq ID NO 9), against templates of genomic DNA of non-transgenic Kentucky Bluegrass, Pp009-401, Pp009-415, and Pp009-469.

The PCR reactions, done in sets of 5 for each primer pair, included the following templates in separate reactions: SEQ ID NO: 1 and 2 were used against 1-μL templates of 10 ng non-transgenic Kentucky Bluegrass cv Abbey from tissue culture, 10 ng Pp009-401, 10 ng Pp009-415, 10 ng Pp009-469, and 1 ng Pp009-401 plus 49.5 ng ea Pp009-415 and Pp009-469 genomic DNA. SEQ ID NO: 3 and 4 were used against 1-μL templates of 10 ng non-transgenic Kentucky Bluegrass cv Abbey from tissue culture, 10 ng Pp009-401, 10 ng Pp009-415, 10 ng Pp009-469, and 1 ng Pp009-415 plus 49.5 ng ea Pp009-401 and Pp009-469 genomic DNA. SEQ ID NO: 5 and 6 were used against 1-μL templates of 10 ng non-transgenic Kentucky Bluegrass cv Abbey from tissue culture, 10 ng Pp009-401, 10 ng Pp009-415, 10 ng Pp009-469, and 1 ng Pp009-469 plus 49.5 ng ea Pp009-401 and Pp009-415 genomic DNA. The PCR conditions used can be found on Table 2. The PCR reactions used the GoTaq®Flexi DNA Polymerase system (Promega Corp, Madison Wis.) (part no M8295) in a 50 μl reaction volume. The colorless 5× GoTaq®Flexi buffer (lacking loading dye) was used. The PCR program was 95° C.-2', (94° C.-45", 65° C.-45", 72° C.-1')x40, 72° C.-10'. After the PCR run, a combination DNA-visualizing agent and loading dye (EZ Vision™ Three 6× Dye and Buffer) (Amresco Inc, Solon, Ohio) (part No N313) was added to each PCR reaction to 1×. Samples of each PCR reaction (15 μL) were then resolved on a 1.3% agarose/TBE gel by electrophoresis, alongside DNA molecular weight markers (Bench Top 100 bp Ladder) (Promega Corp) (Part No G8291), loaded in lanes in between each set.

TABLE 2

PCR conditions for amplification of diagnostic flanking sequences

| | |
|---|---|
| PCR reagents, source | GoTaq ® Flexi DNA Polymerase (Promega Corp, Part # M8295) |
| PCR reaction volume: | 50 μL |
| Template DNA: | 10 ng |
| MgCl2: | 1.5 mM |
| Polymerase: | 1.25 U |
| dNTPs | 200 μM ea |
| PCR buffer | Green or Colorless GoTaq ® Flexi Buffer, to 1 X |
| PCR program: | 95° C. - 2', (94° C. - 45", 65° C. - 45", 72° C. -1') X 40, 72° C. - 10' |

The results are shown in FIG. 8. As expected, the PCR reactions using the primer pair designed to Seq ID NO: 7 (from Pp009-401) amplify a band of expected size (720 bp) from Pp009-401 template, both 10 ng DNA alone, and 1 ng DNA+99 ng mixed DNA of Pp009-401 and 415; and fail to amplify a similar band from either control Abbey, Pp009-415, or Pp009-469 (10 ng ea). Likewise, the PCR reactions using the primer pair designed to SEQ ID NO: 8 (from Pp009-415) amplify a band of expected size (719 bp) from Pp009-415 template, both 10 ng DNA alone, and 1 ng DNA+99 ng mixed DNA of Pp009-401 and 469; and fail to amplify a similar band from either control Abbey, Pp009-401, or Pp009-469 (10 ng ea). Likewise, the PCR reactions using the primer pair designed to SEQ ID NO: 9 (from Pp009-469) amplify a band of expected size (410 bp) from Pp009-469 template, both 10 ng DNA alone, and 1 ng DNA+99 ng mixed DNA of Pp009-401 and 415; and fail to amplify a similar band from either control Abbey, Pp009-401, or Pp009-415 (10 ng ea). These results indicate the transgene/genomic flanking sequences represented in SEQ ID NO: 7, SEQ ID NO: 8, and SEQ ID NO: 9 are unique to their respective transgenic lines.

All publications, patents and patent applications are herein incorporated by reference in their entirety to the same extent as if each individual publication, patent or patent application was specifically and individually indicated to be incorporated by reference in its entirety.

The invention claimed is:

1. A nucleic acid molecule comprising SEQ ID NO: 11 or the complement thereof.

2. A turfgrass plant, plant cell, plant part, or seed comprising the nucleic acid molecule of SEQ ID NO: 11 or the complement thereof.

3. The turfgrass plant part of claim 2, wherein the plant part is a crown, stem, tiller, cutting, apical meristem, pollen, ovule, flower, shoot, stolon, propagule, runner, rhizome, root, or leaf.

4. The turfgrass plant, plant cell, plant part, or seed of claim 2, wherein the turfgrass is bluegrass, St. Augustinegrass, bermudagrass, bentgrass, bahiagrass, centipedegrass, tall fescue, buffalograss, zoysiagrass, ryegrass, or fine fescue.

5. The turfgrass plant, plant cell, plant part, or seed of claim 4, wherein the bluegrass is Kentucky bluegrass.

6. A plasmid comprising the nucleic acid molecule of SEQ ID NO: 11 or the complement thereof.

* * * * *

SEQUENCE LISTING

```
<160> NUMBER OF SEQ ID NOS: 13

<210> SEQ ID NO 1
<211> LENGTH: 29
<212> TYPE: DNA
<213> ORGANISM: Artificial Sequence
<220> FEATURE:
<223> OTHER INFORMATION: Primer

<400> SEQUENCE: 1

gttctgaaaa actgtgcacg tccaagagg                                    29


<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
```

cggccgcggt accatagaat acaga 25

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
ccacacaagc aaacgtcaca aactg 25

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
gcggccgcgg taccacgatt tgcggac 27

<210> SEQ ID NO 5
<211> LENGTH: 31
<212> TYPE: DNA
<213> ORGANISM: Artificial Sequence
<220> FEATURE:
<223> OTHER INFORMATION: Chemically Synthesized

<400> SEQUENCE: 5
caaactagaa ctgcagccac ccgtaaattt g 31

<210> SEQ ID NO 6
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 6
tagacttgag aaacacgacg agtcgct 27

<210> SEQ ID NO 7
<211> LENGTH: 770
<212> TYPE: DNA
<213> ORGANISM: Artificial Sequence
<220> FEATURE:
<223> OTHER INFORMATION: Pp009-401 Event

<400> SEQUENCE: 7
gtatccacac atacgttctg aaaaactgtg cacgtccaag aggtttcttt caatacagag 60
gactgtagtc attatcagct cggaaagctt tctccgcttc ttcatccctc cacctcttct 120
gctcttttta gatgatgtac ggttttgaag cttgtcaacc ttttgtaccc gtgtagaaaa 180
ttttgagttt tcccatgtac tcttctcttt aagaaggcac ggcggcttcc acgaagatgg 240
tggaacaata cggcaaatcc catatggttc tgctgttggc cgtatactct caatatattt 300
tagagtgtct ttaaattcct gatccacgta gagaatatac cataagattg ggctatttag 360
taaaacaaca gagatagata aaacgtgata cggcagttag caaagacgga aggtacctcc 420
tcagtaggat agtagacagg agcttcgtca agaacaggcc tccgtgcacc agctggattc 480
caatttgcag taacctgcat ggtgtgaaaa cacataagac aacaagagac cagcttcatg 540

-continued gaagtaggaa acacaggaat tcagcagacg aatgtgaacc ttttgacagt cactgcagcc 600
tgcacatcct cgaataactc cttttggtaa tttctgtctg cgcttcgctg gacttacagc 660
ctgccaaaag aacattttca tatagtggaa agcattaaaa tcacagtcat ctgtattcta 720
tggtaccgcg gccgcaagct tgtcgacctg atgattattt tgttgatcat 770

<210> SEQ ID NO 8
<211> LENGTH: 832
<212> TYPE: DNA
<213> ORGANISM: Artificial Sequence
<220> FEATURE:
<223> OTHER INFORMATION: Pp009-415

<400> SEQUENCE: 8
gtatcatggt atgggatcac tagatatttt tccacacaag caaacgtcac aaactgccgt 60
ggttcgcatt catccaccaa acacacacac atcatccact gtgctaagca ggcagccaag 120
ctgctgaatg gatgaacagg gatcatgccc gcgtactcca gatcggacag attgatttgg 180
tggcctgttg cggtgcagct gctcgcttgc gtccgtgcgc ggtctgggca gatcaaaaca 240
gggctaggtg gatggctggc tcggctgtcg gctgggcgca ccggcgcagc gaccaaaacg 300
gaggactgga ggaggtgggg acgccctcgc ggacgagcgg agcagaggac cttggcgcgt 360
ggactcccag ccagaccccc ggtgaggcga ggagctgttg gacgttactc gggagcgagc 420
agagcagcga tgctgccgcc gtcggcagcg gagctagggg agcagggaaa gcgccggtga 480
ggagcgggtc ggcagacaac tcaaacgaga agagggagag aggaagaaag gcggcggcgc 540
tcagaactca gatgcgagag gcggggcgac ctgctagtgg acgcggtggt ctgccagcag 600
cgcggcgagg cgaggaagtg agggagggca atggcgtggg gaggcgacac gcacgtgaga 660
ctgtgagaga cggcggcgtt cgctcgcgtt tgggaggaag gcagctaaca attgatcttg 720
tccgtccgca aatcgtggta ccgcggccgc aagctttcta gaatccgaaa agtttctgca 780
ccgttttcac cccctaacta acaatatagg gaacgtgtgc taatataaaa tg 832

<210> SEQ ID NO 9
<211> LENGTH: 516
<212> TYPE: DNA
<213> ORGANISM: Artificial Sequence
<220> FEATURE:
<223> OTHER INFORMATION: Pp009-469

<400> SEQUENCE: 9
tcatcatcgc agcagatgat ggcccaggac ccaggtttcg cgctttgaac tgtgacgctg 60
tgcaagtttg gttgtcaaac tagaactgca gccacccgta aatttgcaag cagcggcaat 120
catgaggtgt gcgacttcag tgtgtcccag ctatcgcgtg tctattgaat ggcgagacct 180
gattcatttt ttaagcatca tggtcctgcc taacttagta ctaatagact gagaatcggg 240
ttgtttgttt tccgaatatg tggaaatttt gtggatcaag gagtagctct tttgagttcc 300
tttgaagttt ggttgattca ggcatctgcg cgtgagagaa caaatgcggc ttgtcatgtc 360
acactcacac cacggacgaa ccaggacaag cagccctcag cccctctatc ccaaccacgg 420
cctcgccggt gatggaccgg gagagtgaga tgctctttag cgactcgtcg tgtttctcaa 480
gtctagatcc gccgccgccg gtaaccaccc cgcccc 516

<210> SEQ ID NO 10
<211> LENGTH: 3456
<212> TYPE: DNA
<213> ORGANISM: Artificial Sequence
<220> FEATURE:
<223> OTHER INFORMATION: EPSPS Cassette

<400> SEQUENCE: 10
acgcgtggta ccgcggccgc aagcttgtcg acctgatgat tattttgttg atcatgattt 60
tcttttggct atttgatttt ttgaaagata tttttttccc tgggaagaca cctatgggac 120
gaagatatta tgttatatat atatatatat atatatcaca tcagtctctg cacaaagtgc 180
atcctgggct gcttcaatta taaagcccca ttcaccacat ttgctagata gtcgaaaagc 240
accatcaata ttgagcttca ggtatttttg gttgtgttgt ggttggattg attctaatat 300
ataccaaatc aatataattc actaccaaaa tataccatag ccatcacaac tttattaatt 360
ttggtagctt aagatggtat atataataac caattaacaa ctgattctaa ttttactacg 420
gcccagtatc taccaataca aaacaacgag tatgttttct tccgtcgtaa tcgtacacag 480
tacaaaaaaa cctggccagc ctttcttggg ctggggctct ctttcgaaag gtcacaaaac 540
gtacacggca gtaacgccgc ttcgctgcgt gttaacggcc accaaccccg ccgtgagcaa 600
acggcatcag ctttccacct cctcgatatc tccgcggcgc cgtctggacc cgcccccttt 660
ccgttccttt ctttccttct cgcgtttgcg tggtggggac ggactcccca aaccgcctct 720
ccctctcttt atttgtctat attctcactg ggccccaccc accgcacccc tgggcccact 780
cacgagtccc cccctcccca cctataaata ccccaccccc tcctcgcctc ttcctccatc 840
aatcgaatcc ccaaaatcgc agagaaaaaa aaatctcccc tcgaagcgaa gcgtcgaatc 900
gccttctcaa gtctagatcc gccgccgccg gtaaccaccc cgcccctctc ctctttcttt 960
ctccgttttt tttttccgtc tcggtctcga tctttggcct tggtagtttg ggtgggcgag 1020
aggcggcttc gtgcgcgccc agatcggtgc gcgggagggg cgggatctcg cggctggggc 1080
tctcgccggc gtggatccgg cccggatctc gcggggaatg gggctctcgg atgtagatct 1140
gcgatccgcc gttgttgggg gagatgatgg ggggtttaaa atttccgcca tgctaaacaa 1200
gatcaggaag aggggaaaag ggcactatgg tttatatttt tatatatttc tgctgcttcg 1260
tcaggcttag atgtgctaga tctttctttc ttctttttgt gggtagaatt tgaatccctc 1320
agcattgttc atcggtagtt tttcttttca tgatttgtga caaatgcagc ctcgtgcgga 1380 gctttttttgt aggtagaagg gatccatggc ccaggtgtcc cgcatctgca acggcgtgca 1440
gaacccatcc ctcatctcca acctctccaa gtcctcccag cgcaagtccc cactctccgt 1500
gtccctcaag acccagcaac acccacgcgc ctacccaatc tccagctcct ggggcctcaa 1560
gaagtccggc atgaccctca tcggctccga gctgcgccca ctcaaggtga tgtcctccgt 1620
gtccaccgcc gagaaggcct ccgagatcgt gctccagcca atccgcgaga tttccggcct 1680
catcaagctc ccaggctcca agtccctctc caaccgcatc ctcctgctcg ccgctctctc 1740
cgagggcacc accgtggtgg acaacctgct caactccgac gacatcaact acatgctcga 1800
cgccctcaag cgcctcggcc tcaacgtgga gaccgactcc gagaacaacc gcgccgtggt 1860
ggagggctgc ggcggcatct tcccagcctc catcgattcc aagtccgaca tcgagctgta 1920
cctcggcaac tccggcacct gcatgaggtc actcacggcg gcggtcaccg cggctggcgg 1980
caacgcctcc tacgtgctcg acggcgtgcc aaggatgcgc gagcgcccaa tcggcgacct 2040
cgtggtgggc ctcaagcaac tcggcgccga cgtggagtgc accctcggca ccaactgccc 2100
accagtgcgc gtgaacgcca acggcggcct cccaggcggc aaggtgaagc tctccggctc 2160
catctcctcc cagtacctca ccgccctgct catgtccgcc ccactcgccc tcggcgacgt 2220
ggagatcgag atcgtggaca agctcatctc cgtgccatac gtggagatga ccctcaagct 2280
catggagcgc ttcggcgtgt ccgtggagca ctccgacagc tgggaccgct tcttcgtgaa 2340
gggcggccag aagtacaagt ccccaggcaa cgcctacgtg gagggcgacg cctcctccgc 2400
ctcctacttc ctcgctggcg ctgccatcac cggcgagacc gtgaccgtgg aggggtgcgg 2460
caccaccagc ctccaaggcg acgtgaagtt cgccgaggtg ctcgagaaga tgggctgcaa 2520
ggtgtcctgg accgagaact ccgtgaccgt gaccggccca ccaagggacg ccttcggcat 2580
gaggcacctc cgcgccatcg acgtgaacat gaacaagatg ccagacgtgg ccatgaccct 2640
cgccgtggtg gccctcttcg ccgacggccc aaccaccatc agggacgtgg ccagctggcg 2700
cgtgaaggag accgagcgca tgatcgccat ctgcaccgag ctgagaaagc tcggcgccac 2760
cgtcgaggag ggctccgact actgcgtgat caccccacca aagaaggtca agaccgccga 2820
gatcgacacc tacgacgacc accgcatggc gatggccttc tccctcgccg cctgcgccga 2880
cgtgccgatc accatcaacg acccaggctg cacccgcaag accttcccag actacttcca 2940
ggtgctcgag cgcatcacca agcactgagc tcgaattcag cttcattgca agctagctcc 3000
tcctgcaggg caggcatgtc gcacagcaaa tgggcatgaa aagttgaagg cgctccagtc 3060
ctccagcttg tgtagtacac agtagcaata aaacgttagt gtttgtcctg tgcccatcct 3120
gtattattct gttccagggt ttcaccttta tcgtcagtgt gtggtcaggt ttcaaccctt 3180
ctcagaacaa ccccctccca gaaaaaaaac aaaggaagaa gtttgtgtcc aggtttcaga 3240
atcccctgtc tgtaattacc attttgcatg acaataatga gatactgtag atattaataa 3300
tgttccagac cttcaaggcc tccctccctc gcaaattgca gatttacttg aggtatcatt 3360
cggtattcac aaaatgtaac gtaaatagta gtgattaaca ctcgattacc agcgataggc 3420
agtttgaata agacggcccg gggcggccgc cccggg 3456

<210> SEQ ID NO 11
<211> LENGTH: 3685
<212> TYPE: DNA
<213> ORGANISM: Artificial Sequence
<220> FEATURE:
<223> OTHER INFORMATION: GAO2X Cassette

<400> SEQUENCE: 11
acgcgtggta ccgcggccgc aagctttcta gaatccgaaa agtttctgca ccgttttcac 60
cccctaacta acaatatagg gaacgtgtgc taaatataaa atgagacctt atatatgtag 120
cgctgataac tagaactatg caagaaaaac tcatccacct actttagtgg caatcgggct 180
aaataaaaaa gagtcgctac actagtttcg ttttccttag taattaagtg ggaaaatgaa 240
atcattattg cttagaatat acgttcacat ctctgtcatg aagttaaatt attcgaggta 300
gccataattg tcatcaaact cttcttgaat aaaaaaatct ttctagctga actcaatggg 360
taaagagaga gatttttttt aaaaaaatag aatgaagata ttctgaacgt attggcaaag 420
atttaaacat ataattatat aattttatag tttgtgcatt cgtcatatcg cacatcatta 480
aggacatgtc ttactccatc ccaattttta tttagtaatt aaagacaatt gacttatttt 540
tattatttat ctttttttcga ttagatgcaa ggtacttacg cacacacttt gtgctcatgt 600
gcatgtgtga gtgcacctcc tcaatacacg ttcaactagc aacacatctc taatatcact 660
cgcctattta atacatttag gtagcaatat ctgaattcaa gcactccacc atcaccagac 720
cacttttaat aatatctaaa atacaaaaaa taattttaca gaatagcatg aaaagtatga 780
aacgaactat ttaggttttt cacatacaaa aaaaaaaaga attttgctcg tgcgcgagcg 840

-continued

```
ccaatctccc atattgggca cacaggcaac aacagagtgg ctgcccacag aacaacccac    900
aaaaaacgat gatctaacgg aggacagcaa gtccgcaaca accttttaac agcaggcttt    960
gcggccagga gagaggagga gaggcaaaga aaaccaagca tcctcctcct cccatctata   1020
aattcctccc cccttttccc ctctctatat aggaggcatc caagccaaga agagggagag   1080
caccaaggac acgcgactag cagaagccga gcgaccgcct tcttcgatcc atatcttccg   1140
gtcgagttct tggtcgatct cttccctcct ccacctcctc ctcacagggt atgtgccctt   1200
cggttgttct tggatttatt gttctaggtt gtgtagtacg ggcgttgatg ttaggaaagg   1260
ggatctgtat ctgtgatgat tcctgttctt ggatttggga tagaggggtt cttgatgttg   1320
catgttatcg gttcggtttg attagtagta tggttttcaa tcgtctggag agctctatgg   1380
aaatgaaatg gtttagggta cggaatcttg cgattttgtg agtacctttt gtttgaggta   1440
aaatcagagc accggtgatt ttgcttggtg taataaaagt acggttgttt ggtcctcgat   1500
tctggtagtg atgcttctcg atttgacgaa gctatccttt gtttattccc tattgaacaa   1560
aaataatcca actttgaaga cggtcccgtt gatgagattg aatgattgat tcttaagcct   1620
gtccaaaatt tcgcagctgg cttgtttaga tacagtagtc cccatcacga aattcatgga   1680
aacagttata atcctcagga acaggggatt ccctgttctt ccgatttgct ttagtcccag   1740
aatttttttt cccaaatatc ttaaaaagtc actttctggt tcagttcaat gaattgattg   1800
ctacaaataa tgcttttata gcgttatcct agctgtagtt cagttaatag gtaatacccc   1860
tatagtttag tcaggagaag aacttatccg atttctgatc tccattttta attatatgaa   1920
atgaactgta gcataagcag tattcatttg gattattttt tttattagct ctcacccctt   1980
cattattctg agctgaaagt ctggcatgaa ctgtcctcaa ttttgttttc aaattcacat   2040
cgattatcta tcgattatcc tcttgtatct acctgtagaa gtttcttttt ggttattcct   2100
tgactgcttg attacagaaa gaaatttatg aagctgtaat cgggatagtt atactgcttg   2160
ttcttatgat tcatttcctt tgtgcagttc ttggtgtagc ttgccacttt caccagcaaa   2220
gtttcggatc catggcctcc accaaggtgg tcgagcacct caaggagaac gtcctctgga   2280
agcaggccat catggaccgc aacgccaaca tctccgaccc accgttcgag gagacctaca   2340
agaacctcct gctcaagcac aacatcaccc cgctcaccac caccacgacc acgacgacca   2400
ccacggcgac catcgaggtg agggatctcc cactcatcga cctctccagg ctcgtggcca   2460
ccgccgccaa ggagcgcgag aactgcaaga gggatatcgc caacgcctcc cgcgagtggg   2520
gcttcttcca ggtggtgaac cacggcatcc cgcataggat gctcgaggag atgaacaagg   2580
agcaggtcaa ggtgttccgc gagccgttca acaagaagaa gggcgacaac tgcatgaacc   2640
tcaggctctc cccaggctcc tacaggtggg gctccccgac cccgaactgc ctctcccagc   2700
tctcctggtc cgaggccttc cacatcccga tgaacgacat ctgctccaac gccccgagga   2760
acattgccaa cggcaacccg aacatctcca acctctgctc caccgtgaag cagttcgcca   2820
ccaccgtgtc cgagctggcc aacaagctcg ccaacatcct cgtcgagaag ctcggccatg   2880
acgagctgac cttcatcgag gagaagtgct ccccgaacac gtgctacctc aggatgaacc   2940
gctacccgcc gtgcccaaag tactcccacg tgctcggcct catgccacat accgactccg   3000
acttcctcac catcctctac caggaccagg tgggcggcct ccagctcgtg aaggacggcc   3060
gctggatttc cgtgaagccg aacccagagg ccctcatcgt gaacatcggc gacctcttcc   3120
aggcctggtc taacggcgtg tacaagtccg tggtgcatag ggtggtggcc aacccgaggt   3180
```

-continued

```
tcgagaggtt ctctaccgcc tacttcctct gcccgtccgg cgacgccgtg atccagtcct   3240

accgcgagcc gtctatgtac cgcaagttca gcttcggcga gtacaggcag caggtccagc   3300

aggacgtgcg cgagttcggc cacaagatcg gcctctcccg cttcctcatc tgcaagagct   3360

cgaattcgca tggcgtggga taatacagac tgtatatagg aggaataatg gtttgctgct   3420

tgtagctctg taaataggaa aatgaagctc agcttttact ttcagtcatc tagttcggta   3480

gtgtaggtcg ggtttgctga agtttggtta atgaaggctc tgtgtctctg caaattaagg   3540

cgttgttctg tcaataatca tctttttttct gcaacatgct ttctttcaaa tttgccgagt   3600

tacttttgta atgatcatta atggcattgt ataatcattg attggtcgac gataatcaat   3660

tgcctgtatc acaaattcaa gactt                                          3685
```

<210> SEQ ID NO 12
<211> LENGTH: 1557
<212> TYPE: DNA
<213> ORGANISM: Artificial Sequence
<220> FEATURE:
<223> OTHER INFORMATION: EPSPS variant

<400> SEQUENCE: 12

```
cccaggtgtc ccgcatctgc aacggcgtgc agaacccatc cctcatctcc aacctctcca     60

agtcctccca gcgcaagtcc ccactctccg tgtccctcaa gacccagcaa cacccacgcg    120

cctacccaat ctccagctcc tggggcctca agaagtccgg catgaccctc atcggctccg    180

agctgcgccc actcaaggtg atgtcctccg tgtccaccgc cgagaaggcc tccgagatcg    240

tgctccagcc aatccgcgag atttccggcc tcatcaagct cccaggctcc aagtccctct    300

ccaaccgcat cctcctgctc gccgctctct ccgagggcac caccgtggtg gacaacctgc    360

tcaactccga cgacatcaac tacatgctcg acgccctcaa gcgcctcggc ctcaacgtgg    420

agaccgactc cgagaacaac cgcgccgtgg tggagggctg cggcggcatc ttcccagcct    480

ccatcgattc caagtccgac atcgagctgt acctcggcaa ctccggcacc tgcatgaggt    540

cactcacggc ggcggtcacc gcggctggcg gcaacgcctc ctacgtgctc gacggcgtgc    600

caaggatgcg cgagcgccca atcggcgacc tcgtggtggg cctcaagcaa ctcggcgccg    660

acgtggagtg caccctcggc accaactgcc caccagtgcg cgtgaacgcc aacggcggcc    720

tcccaggcgg caaggtgaag ctctccggct ccatctcctc ccagtacctc accgccctgc    780

tcatgtccgc cccactcgcc ctcggcgacg tggagatcga gatcgtggac aagctcatct    840

ccgtgccata cgtggagatg accctcaagc tcatggagcg cttcggcgtg tccgtggagc    900

actccgacag ctgggaccgc ttcttcgtga agggcggcca gaagtacaag tccccaggca    960

acgcctacgt ggagggcgac gcctcctccg cctcctactt cctcgctggc gctgccatca   1020

ccggcgagac cgtgaccgtg gaggggtgcg gcaccaccag cctccaaggc gacgtgaagt   1080

tcgccgaggt gctcgagaag atgggctgca aggtgtcctg gaccgagaac tccgtgaccg   1140

tgaccggccc accaagggac gccttcggca tgaggcacct ccgcgccatc gacgtgaaca   1200

tgaacaagat gccagacgtg gccatgaccc tcgccgtggt ggccctcttc gccgacggcc   1260

caaccaccat cagggacgtg gccagctggc gcgtgaagga gaccgagcgc atgatcgcca   1320

tctgcaccga gctgagaaag ctcggcgcca ccgtcgagga gggctccgac tactgcgtga   1380

tcaccccacc aaagaaggtc aagaccgccg agatcgacac ctacgacgac caccgcatgg   1440

cgatggcctt ctccctcgcc gcctgcgccg acgtgccgat caccatcaac gacccaggct   1500

gcacccgcaa gaccttccca gactacttcc aggtgctcga gcgcatcacc aagcact      1557
```

-continued

```
<210> SEQ ID NO 13
<211> LENGTH: 1125
<212> TYPE: DNA
<213> ORGANISM: Artificial Sequence
<220> FEATURE:
<223> OTHER INFORMATION: GA02X transgene

<400> SEQUENCE: 13

atggcctcca ccaaggtggt cgagcacctc aaggagaacg tcctctggaa gcaggccatc     60

atggaccgca acgccaacat ctccgaccca ccgttcgagg agacctacaa gaacctcctg    120

ctcaagcaca acatcacccc gctcaccacc accacgacca cgacgaccac cacggcgacc    180

atcgaggtga gggatctccc actcatcgac ctctccaggc tcgtggccac cgccgccaag    240

gagcgcgaga actgcaagag ggatatcgcc aacgcctccc gcgagtgggg cttcttccag    300

gtggtgaacc acggcatccc gcataggatg ctcgaggaga tgaacaagga gcaggtcaag    360

gtgttccgcg agccgttcaa caagaagaag ggcgacaact gcatgaacct caggctctcc    420

ccaggctcct acaggtgggg ctccccgacc ccgaactgcc tctcccagct ctcctggtcc    480

gaggccttcc acatcccgat gaacgacatc tgctccaacg ccccgaggaa cattgccaac    540

ggcaacccga acatctccaa cctctgctcc accgtgaagc agttcgccac caccgtgtcc    600

gagctggcca acaagctcgc caacatcctc gtcgagaagc tcggccatga cgagctgacc    660

ttcatcgagg agaagtgctc cccgaacacg tgctacctca ggatgaaccg ctacccgccg    720

tgcccaaagt actcccacgt gctcggcctc atgccacata ccgactccga cttcctcacc    780

atcctctacc aggaccaggt gggcggcctc cagctcgtga aggacggccg ctggatttcc    840

gtgaagccga acccagaggc cctcatcgtg aacatcggcg acctcttcca ggcctggtct    900

aacggcgtgt acaagtccgt ggtgcatagg gtggtggcca acccgaggtt cgagaggttc    960

tctaccgcct acttcctctg cccgtccggc gacgccgtga tccagtccta ccgcgagccg   1020

tctatgtacc gcaagttcag cttcggcgag tacaggcagc aggtccagca ggacgtgcgc   1080

gagttcggcc acaagatcgg cctctcccgc ttcctcatct gcaac                   1125
```